United States Patent
Kumar et al.

(10) Patent No.: US 9,284,341 B2
(45) Date of Patent: Mar. 15, 2016

(54) RAPIDLY DISSOLVING PHARMACEUTICAL COMPOSITION

(71) Applicant: UNIVERSITY OF THE WITWATERSRAND, JOHANNESBURG, Johannesburg (ZA)

(72) Inventors: Pradeep Kumar, Johannesburg (ZA); Viness Pillay, Sandton (ZA); Yahya Essop Choonara, Johannesburg (ZA)

(73) Assignee: UNIVERSITY OF THE WITWATERSRAND, Johannesburg (ZA)

( * ) Notice: Subject to any disclaimer, the term of this patent is extended or adjusted under 35 U.S.C. 154(b) by 0 days.

(21) Appl. No.: 14/427,244

(22) PCT Filed: Sep. 11, 2013

(86) PCT No.: PCT/IB2013/058458
§ 371 (c)(1),
(2) Date: Mar. 10, 2015

(87) PCT Pub. No.: WO2014/041489
PCT Pub. Date: Mar. 20, 2014

(65) Prior Publication Data
US 2015/0274765 A1    Oct. 1, 2015

(30) Foreign Application Priority Data

Sep. 11, 2012 (ZA) .................. 2012/06792
Sep. 11, 2012 (ZA) .................. 2012/06803

(51) Int. Cl.
| | | |
|---|---|---|
| *C07H 15/02* | (2006.01) | |
| *A61K 9/00* | (2006.01) | |
| *A61K 31/5377* | (2006.01) | |
| *A61K 31/196* | (2006.01) | |
| *A61K 31/138* | (2006.01) | |
| *A61K 31/4196* | (2006.01) | |
| *A61K 45/06* | (2006.01) | |
| *A61K 9/20* | (2006.01) | |

(52) U.S. Cl.
CPC .............. *C07H 15/02* (2013.01); *A61K 9/0051* (2013.01); *A61K 9/2013* (2013.01); *A61K 9/2027* (2013.01); *A61K 9/2031* (2013.01); *A61K 9/2054* (2013.01); *A61K 9/2059* (2013.01); *A61K 9/2077* (2013.01); *A61K 9/2095* (2013.01); *A61K 31/138* (2013.01); *A61K 31/196* (2013.01); *A61K 31/4196* (2013.01); *A61K 31/5377* (2013.01); *A61K 45/06* (2013.01); *A61K 9/2072* (2013.01)

(58) Field of Classification Search
CPC .............. A61K 31/138; A61K 31/196; A61K 31/4196; A61K 31/5377; A61K 45/06; A61K 9/0051; A61K 9/2013; A61K 9/2027; A61K 9/2031; A61K 9/2054; A61K 9/2059; A61K 9/2072; A61K 9/2077; A61K 9/2095
See application file for complete search history.

(56) References Cited

U.S. PATENT DOCUMENTS

2005/0065175 A1   3/2005  Gonzales et al.

FOREIGN PATENT DOCUMENTS

| SE | WO 9826788 A1 * | 6/1998 | ............. A61K 8/736 |
|---|---|---|---|
| WO | WO 98/26788 A1 | 6/1998 | |
| WO | WO 2009/153634 A1 | 12/2009 | |
| WO | WO 2012/083269 A1 | 6/2012 | |

* cited by examiner

*Primary Examiner* — Wu-Cheng Winston Shen
*Assistant Examiner* — Jean Cornet
(74) *Attorney, Agent, or Firm* — Ladas & Parry LLP

(57) ABSTRACT

The present invention relates to a pharmaceutical dosage form which may comprise carbamoyl glycinated chitosan, and particularly it relates to a pharmaceutical dosage form comprising the novel polymer in a lyophilized polymeric wafer form which shows rapid disintegration and dissolution characteristics in use.

19 Claims, 21 Drawing Sheets

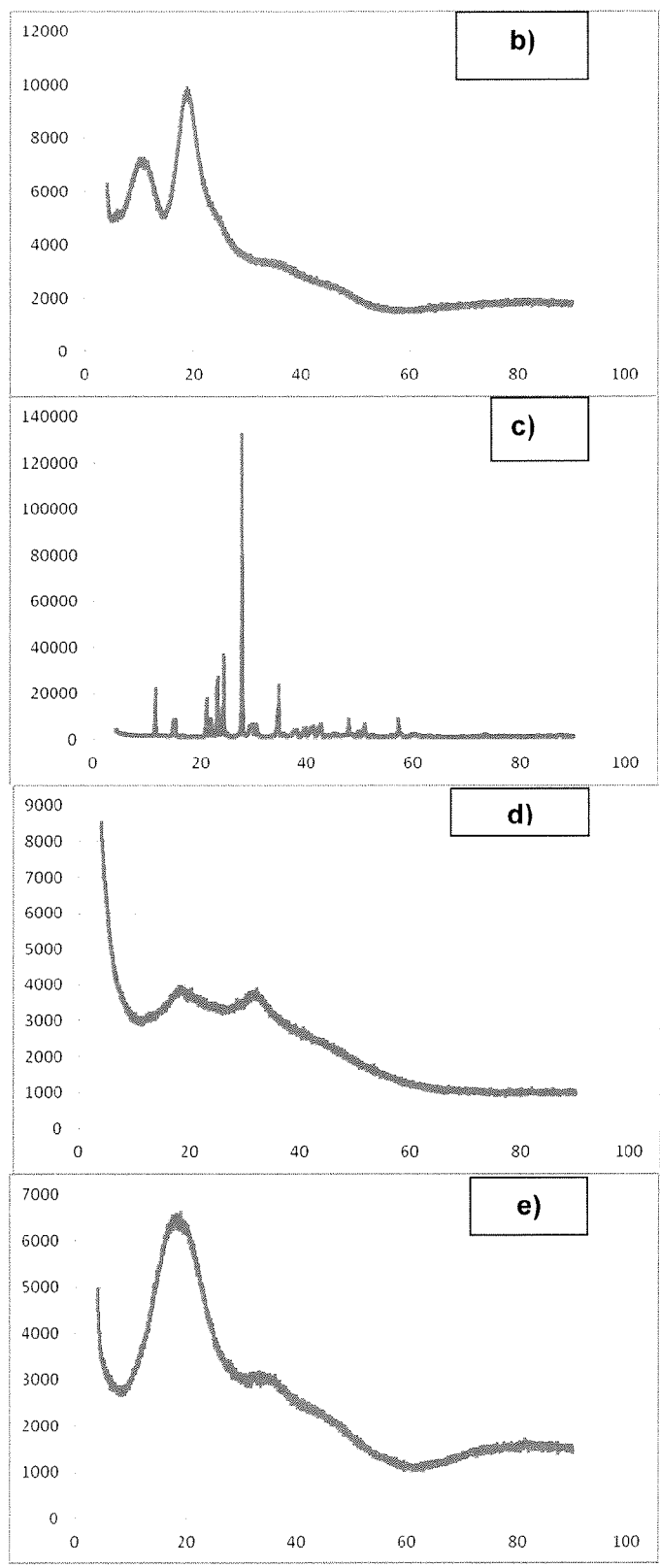
FIGURES 18 b-e

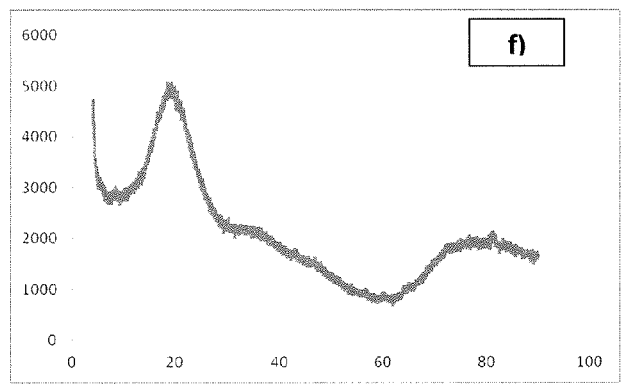
FIGURE 18 f
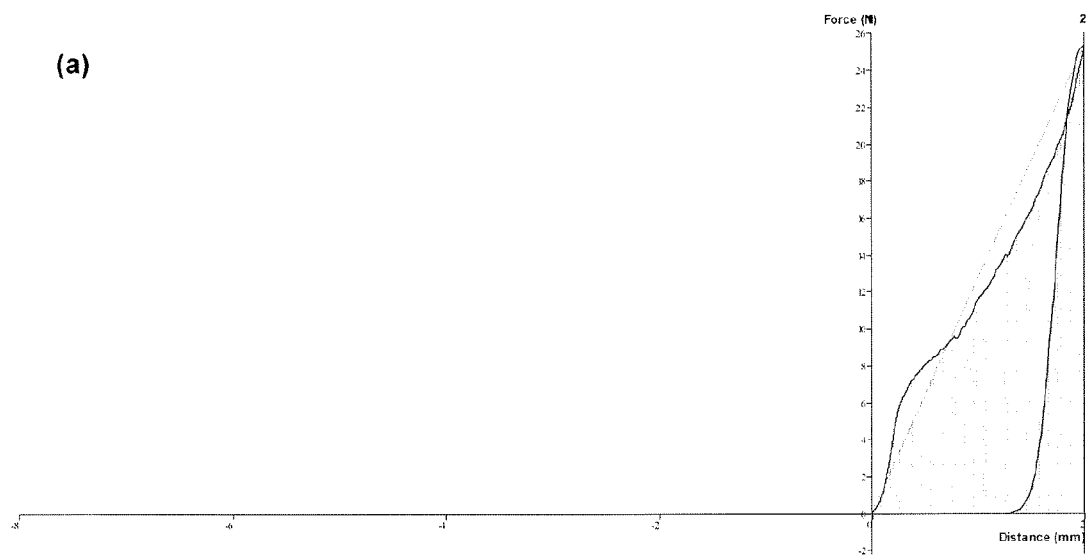
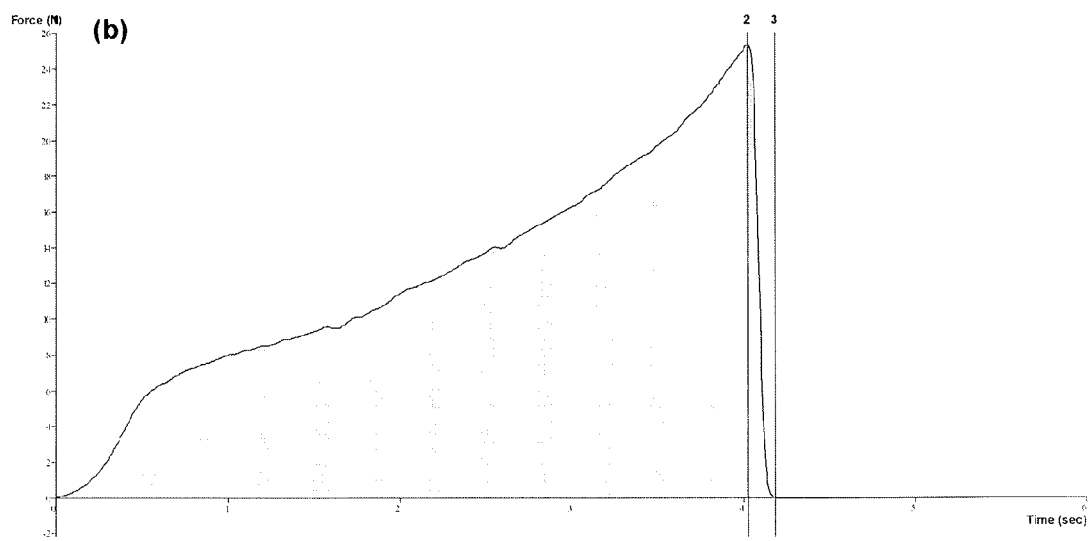
FIGURE 19 a-b

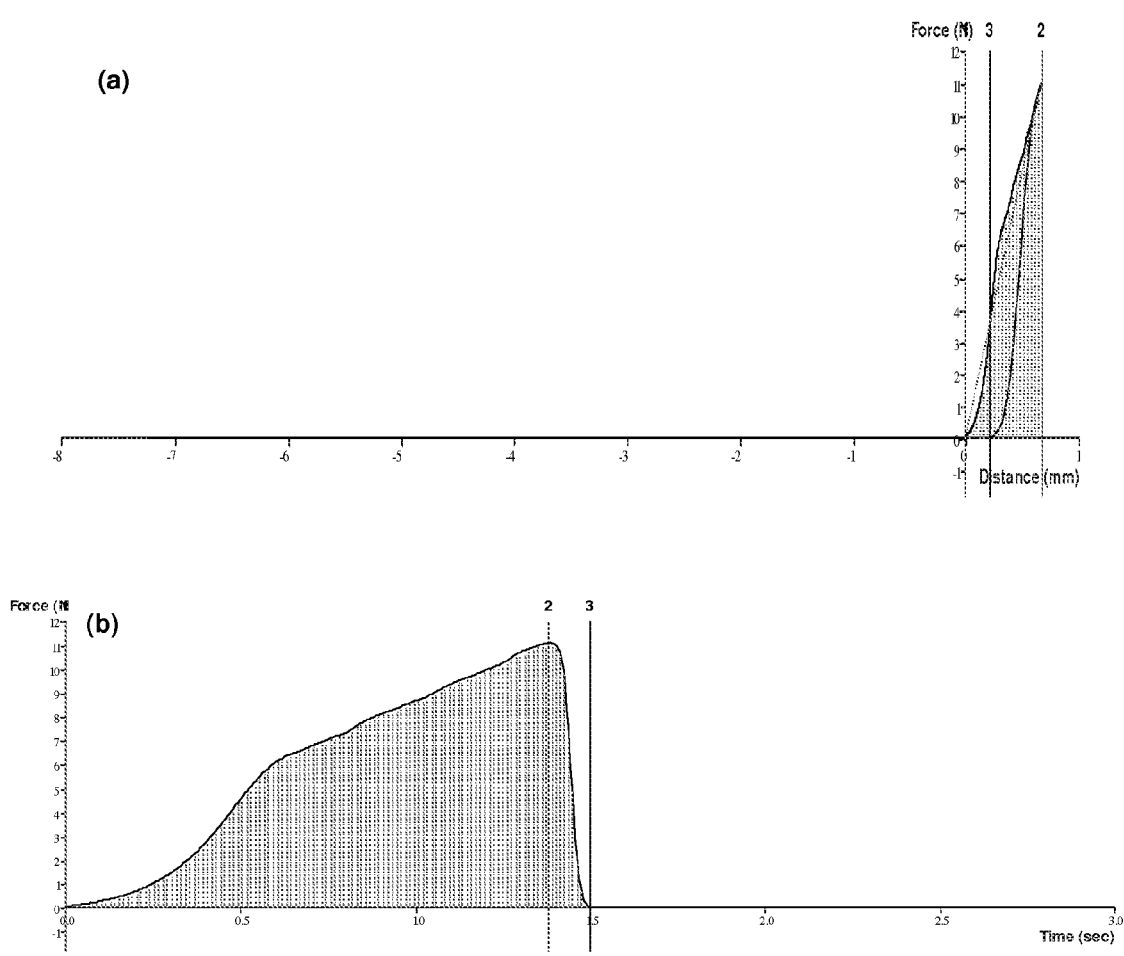
FIGURE 20 a-b

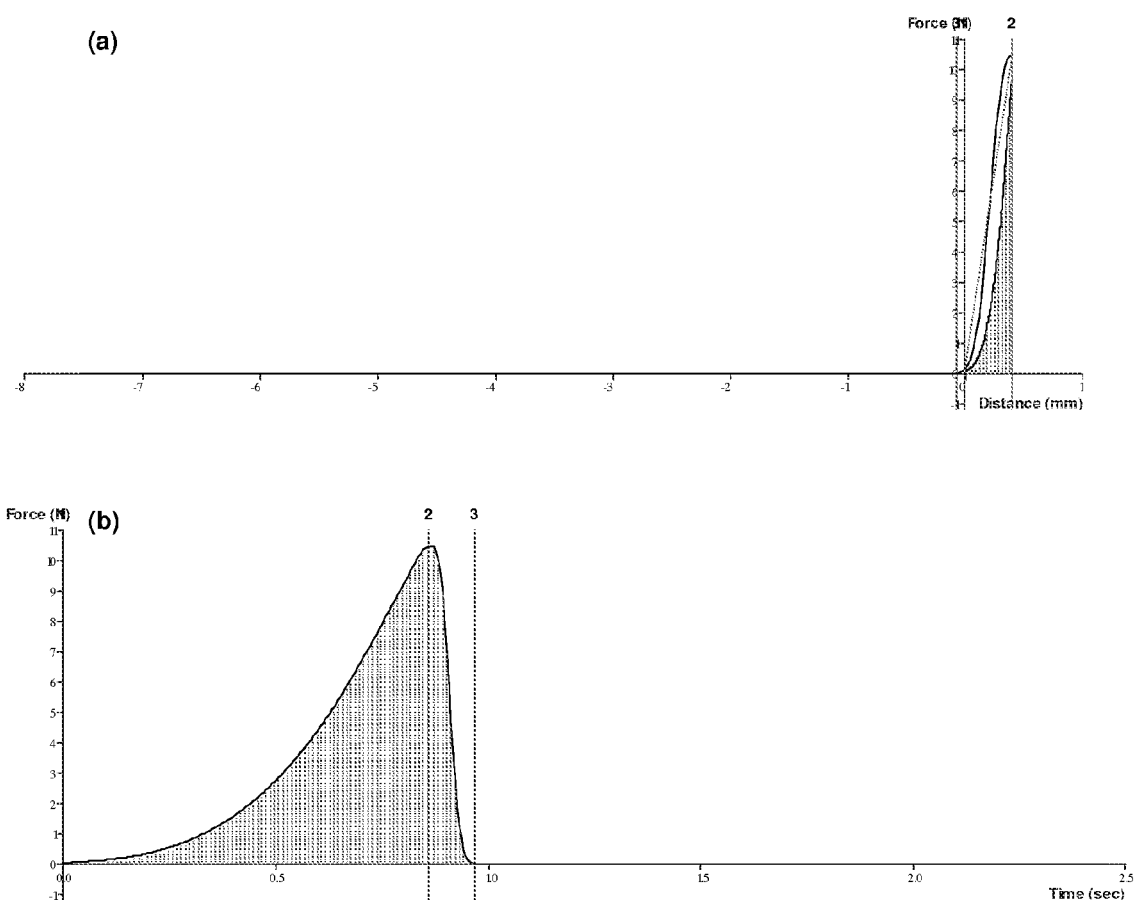
FIGURE 21 a-b

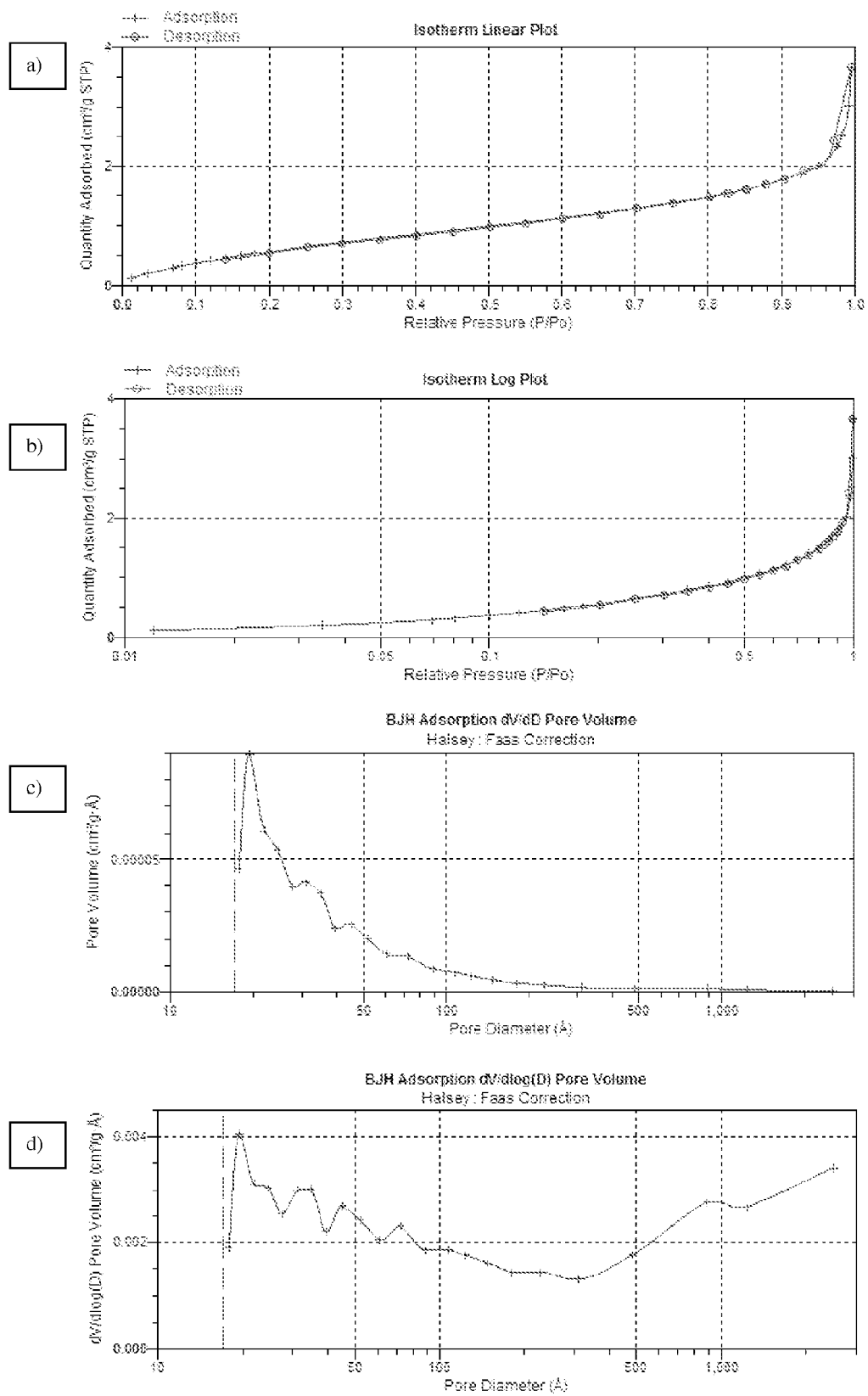
FIGURE 22 a-d

RAPIDLY DISSOLVING PHARMACEUTICAL COMPOSITION

RELATED APPLICATION

This application is a national phase entry under 35 USC 371 of International Patent Application No PCT/IB2013/058458 filed on 11 Sep. 2013, which claims priority from South African Patent Application Nos. 2012/06803 filed on 11 Sep. 2012 and 2012/06792 filed on 11 Sep. 2012, the disclosures of which are incorporated in their entirety by reference herein.

FIELD OF THE INVENTION

The present invention relates to a pharmaceutical dosage form which may comprise a novel polymer, and particularly it relates to a pharmaceutical dosage form comprising the novel polymer in a lyophilized polymeric wafer form which shows rapid disintegration and dissolution characteristics in use.

BACKGROUND TO THE INVENTION

Successful treatment of medical conditions and/or disease is not only dependent on novel active pharmaceutical ingredients (API), but it is also dependent on providing novel and effective pharmaceutical dosage forms to ensure delivery of the API to the intended target site within the human or animal being treated. In order to achieve effective API delivery at the intended site due consideration must be given to where the intended target is within the body, and to the physiological obstacles that may prevent effective delivery via various routes of administration.

Often the time taken for the API to reach its target site is also important. This is of particular importance in API's that provide pain relief or allergy relief.

Extensive research has been conducted in the field of biocompatible polymers which have been developed to provide effective pharmaceutical dosage forms. These polymers are then formulated into various solid dosage forms such as wafers, tablets and capsules depending on their physico-chemical and/or physico-mechanical properties.

Wafer technology is already used within the pharmaceutical industry as a species of pharmaceutical dosage form. Wafers are typically used when needing to deliver API through the mucosal membrane of the mouth cavity. Essentially, the wafer incorporates at least one active pharmaceutical ingredient (API) to be released in use. When formulating wafers, one needs to consider several variables, including, but not limited to the fact that: the API should be rapidly absorbed through the mucosal membranes in the mouth via transmucosal absorption; wafer technologies typically attempt to deliver API's that cannot be effectively delivered via conventional oral solid dosage (OSD) forms (for reasons including that the API has a low gastric bioavailability, and that normal OSD's may result in nausea of the patient making them unsuitable); a low dose of the API is typically required since the dosage form is not subjected to passage through the entire gastro-intestinal tract; and rapid action is often required, especially where pain and/or allergy relief is required.

Known wafer technology typically relies on the formulation of the active pharmaceutical ingredient (API) within a water soluble polymeric/excipient blend to dissolve rapidly in the mouth, thereby releasing the API for absorption and transport to its desired target. To be effective, the formulation requires that the following performance aspects are met: the polymers and/or excipients used to manufacture the wafer must be soluble at physiological temperature (about 37 qC) without the aid of heating or stirring; the API taste must be masked by the excipients; the wafer should not be excessively hygroscopic and must have an acceptable shelf life; the total wafer size should not exceed a diameter of about 2 cm and the mass should be less than about 800 mg for ease of use for the patient; and the wafers should dissolve completely and leave no residue after disintegration.

The manufacture of rapidly dissolving dosage forms, particularly wafer type dosage forms, for the rapid release of active pharmaceutical ingredient remains a difficult task. The lyophilized polymeric matrices of the dosage forms are not robust and present difficulty in handling with a risk of breaking when taking them out from the packaging (typically blister packs). Therefore, a specialized peel-off packaging is required for the same which further increases that final cost of the product. The complete solubility of the matrix components is very important as a gritty feel would compromise patient compliance. The disintegration, dispersion, and dissolution of the matrix should be very fast in order to provide enhanced permeability and taste-masking.

Existing products on the market include the Zydis® technology, which has been used for a number of commercial products including Claritin® Reditab®, Dimetapp® Quick Dissolve, Feldene® Melt, Maxalt-MLT®, Pepcid® RPD, Zofran® ODT®, and Zyprexa®. The existing products are known to use active pharmaceutical ingredients (APIs) including for examples: oxazepam, lorazepam, loperamide, and enalapril.

There is a need for novel and improved pharmaceutical dosage forms in order to improve effective delivery of APIs.

SUMMARY OF THE INVENTION

According to a first aspect of the invention there is provided a pharmaceutical dosage form for the release of at least one active pharmaceutical ingredient (API) at a target site in a human or animal, the pharmaceutical dosage form comprising:

a compound of the Formula (I):

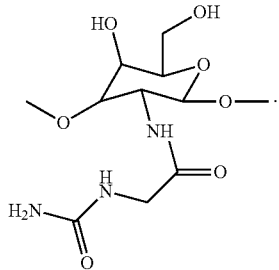

Formula (I)

The compound of the Formula (I) is a soluble ester derivative of chitosan and is herein termed carbamoyl glycinated chitosan (CmGC). The compound of the Formula (I) may be polymeric.

The pharmaceutical dosage form may further comprise a soluble matrix forming polymer.

The soluble matrix forming polymer may be at least one natural and/or synthetic polymer selected from the group including, but not limited to: polyanionic polysaccharides, carboxymethyl cellulose, carboxymethyl amylose, chondroitin-6-sulfate, dermatin sulfate, heparin, heparin sulfate, collagen, fibrinogen, albumin, fibrin, chitosan, hyaluronic acid, polyvinylpyrrolidone, polyvinyl alcohol) and its derivatives, poly(ethylene glycol) and its derivatives, pluronics, poloxamers, tetronics, polybutylene oxide, poly(ethylene oxide), polypropylene oxide), poly(ethylene oxide)-poly (propylene oxide)-poly(ethylene oxide), poly(vinyl acetate), polyvinyl amine), pectin, carrageenan, dextran sulfate, polylysine, gelatin, carboxymethyl chitin, dextran, agarose, and pullulan.

In a preferred embodiment of the invention, the soluble matrix forming polymer may be a starch derivative, particularly a hydroxyalkylated starch derivative, more preferably hydroxypropyl cellulose (HPC).

The pharmaceutical dosage form may further comprise at least one ester containing derivative of an acrylic polymer selected from the group including, but not limited to: poly (hydroxyethyl methylacrylate), hydroxypropyl methacrylamide-based copolymers, polyacrylamide, poly(methacrylic acid-grafted-ethylene glycol), poly(N-2-hydroxypropyl methacrylamide), poly(2-hydroxyethylmethacrylate), poly (acrylic acid), poly-acrylamide, polyacrylonitrile, polycaprolactone, poly(ethylene imine), poly(ethyl methacrylate), propylene fumarate, poly(glucosylethyl methacrylate), poly (hydroxy butyrate), poly(hydroxyethyl methacrylate), poly (hydroxypropyl methacrylamide), and poly(methyl methacrylate) and their polyesters.

In a preferred embodiment of the invention, the ester containing derivative of an acrylic polymer may be an ester derivative of polyacrylic acid, more preferably sodium polyacrylate.

The pharmaceutical dosage form may further comprise an anti-collapsing agent. The anti-collapsing agent may comprise an amino acid chain, preferably the amino acid chain having 1 amino acid residue, more preferably 2 amino acid residues.

In a preferred embodiment of the invention, the anti-collapsing agent comprises an amino acid chain having two amino acid residues, preferably diglycine.

The pharmaceutical dosage form may further comprise at least one filler substance, in use binding and/or combining the various components comprising the dosage form, the filler substance may be at least one compound selected from the group including, but not limited to: maltodextrin (MD), dextrin; alkaline-modified starch; bleached starch; oxidized starch, enzyme-treated starch such as maltodextrin, cyclodextrin, monostarch phosphate, distarch phosphate by esterification, crosslinked starch, acetylated starch, hydroxypropylated starch, hydroxyethyl starch, cationic starch, carboxymethylated starch, phosphated distarch phosphate, hydroxypropyl distarch phosphate, acetylated oxidized starch. In a preferred embodiment of the invention, the starch derivative comprises an enzyme treated/hydrolyzed starch, more preferably maltodextrin.

The pharmaceutical dosage form may further comprise at least one taste masking agent, in use to mask the unsavoury taste of the dosage form, the taste masking agent may be selected from the group including, but not limited to: macrocyclic compound such as but not limited to: cyclodextrins and their derivatives, porphyrins, ion exchange resins and cucurbiturils, permeation enhancing agents well known in the art such as surfactants (fatty acid derivatives—for example: sodium decanoate), and stabilizers.

In a preferred embodiment of the invention, the cyclodextrin derivative comprises a rapidly soluble derivative, more preferably hydroxypropyl-beta-cyclodextrin (HPβCD). It is to be understood that the taste masking agent may also act in use as a permeation enhancer.

The pharmaceutical dosage form may further comprise an active pharmaceutical ingredient (API). The API may be selected from the group including, but not limited to: smoking cessation drugs, narcotic analgesics, anesthetics, antitussives, normarcotic analgesics such as the nonsteroidal anti-inflammatory agents (NSAIDS), erectile dysfunction drugs, female sexual dysfunction drugs, antihistamines, cold and allergy drugs, drugs that combat cough, drugs that combat respiratory disorders, drugs that combat sore throat, drugs that combat heartburn and/or dyspepsia, antiemetics, sleep aids, drugs that combat diarrhea, drugs that improve oral hygiene, antagonists of CGRP receptors, drugs associated with migraine treatment, drugs for hormone replacement, drugs that combat Alzheimer's disease, sitagliptin, caffeine and caffeine salt compounds.

The API may be incorporated together with at least one of the compound of Formula (I) and/or the soluble matrix forming polymer and/or the ester containing derivative of the acrylic acid and/or the anti-collapsing agent and/or the filler substance and/or the taste masking agent. API incorporation may take place via at least one of the group including, but not limited to: non-covalent interactions, covalent interactions, van der Waals forces, electrostatic interactions and hydrogen bonding.

The active pharmaceutical ingredient (API) may be incorporated within the taste masking agent hydroxypropyl-beta-cyclodextrin (HPβCD) to form a HPβCD-API inclusion complex.

An embodiment of the invention may be formulated as a placebo and lacking an API. Such a placebo embodiment may comprise:
- a compound of Formula (I), (carbamoyl glycinated-chitosan);
- a soluble matrix forming polymer, preferably hydroxypropyl cellulose (HPC);
- an ester containing derivative of an acrylic polymer, preferably sodium polyacrylate;
- an anti-collapsing agent, preferably diglycine; and
- a filler substance, preferably maltodextrin.

In a preferred embodiment of the invention the pharmaceutical dosage form may comprise:
- a compound of Formula (I), (carbamoyl glycinated-chitosan);
- a soluble matrix forming polymer, preferably hydroxypropyl cellulose (HPC);
- an ester containing derivative of an acrylic polymer, preferably sodium polyacrylate;
- an anti-collapsing agent, preferably diglycine;
- a filler substance, preferably maltodextrin; and
- a taste masking agent and API, preferably HPβCD-API inclusion complex.

In a preferred embodiment of the invention the pharmaceutical dosage form is formed into a wafer to be applied in use to mucosa lining the oral cavity of a human or animal.

In another embodiment of the invention the pharmaceutical dosage form is formed into a tablet, alternatively a capsule, further alternatively a solid ocular dosage form.

It is important to understand that the pharmaceutical dosage form according to this invention may be formulated as an oral wafer matrix, a graft lubricant, a chromatography gel, a wound dressing, a mesh, a degradable bone fixation glue, a degradable ligament glue and sealant, a tendon implant, a dental implant, a reconstituted nerve injectable, a disposable article, a disposable contact lens, an ocular device, a rupture net, a rupture mesh, an instant blood bag additive, an instant haemodialysis additive, an instant peritoneal dialysis additive, an instant plasmapheresis additive, an inhalation drug delivery device, a cardiac assist device, a tissue replacing implant, a drug delivery device, an endotracheal tube lubricant, a drain additive, and a dispersible suspension system.

There is provided that the dosage form according to the invention, especially in regard to a watered dosage form, incorporates advantages such as the fact that no coating or microencapsulation is involved; there is a one-step formulation; no effervescence in use; robust and non-friable formulation (for geriatrics); no moisture sensitivity; no chewing required; no water insoluble content; no grittiness; and no remnants after and/or during use.

According to a second aspect of the invention there is provided a pharmaceutical dosage form for the release of at least one active pharmaceutical ingredient (API) at a target site in a human or animal, the pharmaceutical dosage form comprising a soluble matrix forming polymer, an ester containing derivative of an acrylic polymer, an anti-collapsing agent, and a filler substance.

The pharmaceutical dosage form according to the second aspect of the invention, wherein the soluble matrix forming polymer may be of the class of cellulosic polymers, preferably hydroxypropyl cellulose, wherein the ester containing derivative of an acrylic polymer may be sodium polyacrylate, wherein the anti-collapsing agent may be diglycine, and wherein the filler substance may by maltodextrin.

The second aspect of the invention may further comprise at least one active pharmaceutical compound (API).

The second aspect of the invention may further comprise a taste masking agent.

The second aspect of the invention may further comprise a taste masking agent and API, preferably hydroxypropyl-beta-cyclodextrin HPβCD-active pharmaceutical ingredient (API) inclusion complex (HPβCD-API inclusion complex).

An embodiment of the invention may be formulated as a placebo and lacking an API. Such a placebo embodiment may comprise:

a soluble matrix forming polymer, preferably hydroxypropyl cellulose (HPC);

an ester containing derivative of an acrylic polymer, preferably sodium polyacrylate;

an anti-collapsing agent, preferably diglycine; and a filler substance, preferably maltodextrin.

The placebo may further comprise a taste-masking agent, preferably HPβCD.

In a preferred embodiment of the second aspect of the invention the pharmaceutical dosage form may comprise:

a soluble matrix forming polymer, preferably hydroxypropyl cellulose (HPC);

an ester containing derivative of an acrylic polymer, preferably sodium polyacrylate;

an anti-collapsing agent, preferably diglycine;

a filler substance, preferably maltodextrin; and a taste masking agent and API, preferably HPβCD-API inclusion complex.

There is provided that the dosage forms according to this invention may be homogenous, alternatively layered like a sandwich, alternatively layered like an onion. In the event that the dosage form is layered, each layer may include at least one of the same or different API.

According to a third aspect of the invention there is provided a compound of the Formula (I):

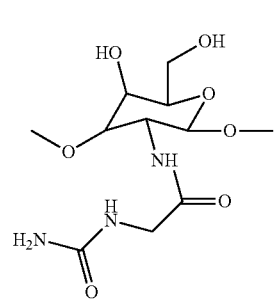

Formula (I)

The compound of Formula (I) is herein termed carbamoyl glycinated chitosan. The compound may be polymeric.

According to a fourth aspect of the invention there is provided a method of manufacturing the compound of Formula (I) of the third aspect of this invention, herein termed carbamoyl glycinated chitosan, the method comprising the steps of:

(a). dissolving chitosan in a hydantoic acid solution;
(b). dialyzing said solution;
(c). freezing said dialyzed solution; and
(d). lyophilizing the frozen solution.

The method of manufacturing the compound of Formula (I) may take place via the following reaction:

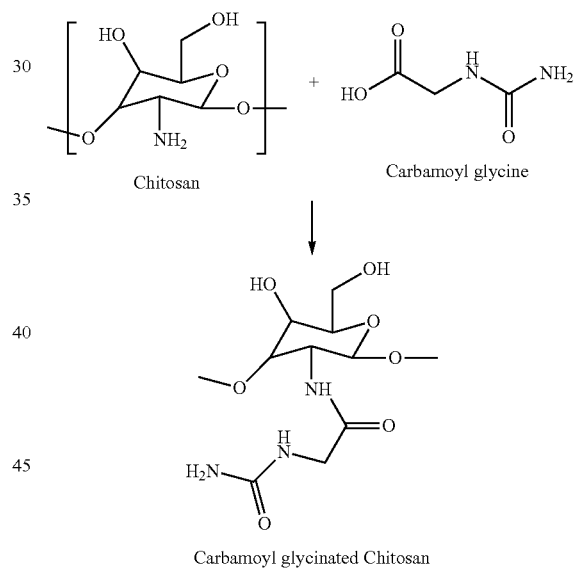

Carbamoyl glycinated Chitosan

Prior to Step (b) the solution may be centrifuged to remove any or all particulate matter. The centrifuged solution may be dialyzed against water, preferably deionized water.

Step (c) may take place at about −82° C. for a certain period of time, preferably about 24 to about 48 hours.

Lyophilization may take place at about 25 mtorr, about −42° C., for about 12 to about 48 hours.

After Step (d) the carbamoyl glycinated chitosan may be pulverised and stored for use. Storage may be in a desiccator.

According to a fifth aspect of the invention there is provided a method of manufacturing the pharmaceutical dosage form of the first aspect of this invention, the method comprising the steps of:

(a), dissolving a soluble matrix forming polymer, preferably hydroxy propyl cellulose (HPC), in a liquid medium, preferably deionized water to produce Solution 1;

(b). adding to Solution 1 a soluble chitosan derivative polymer, preferably the carbamoyl glycinated chitosan of the first aspect of the invention, to produce Solution 2;

(c). adding to Solution 2 a filler, preferably maltodextrin, an ester containing derivative of an acrylic polymer, preferably sodium polyacrylate and an anti-collapsing agent, preferably diglycine, to produce Solution 3;

(d). adding to Solution 3 a taste-masking agent and API, preferably HPβCD-API inclusion complex, to produce Solution 4;

(e). freezing Solution 4; and (f). lyophilizing the frozen Solution 4.

According to a sixth aspect of the invention there is provided a method of manufacturing the pharmaceutical dosage form of the second aspect of this invention, the method comprising the steps of:

(a), dissolving a soluble matrix forming polymer, preferably hydroxy propyl cellulose (HPC), in a liquid medium, preferably deionized water to produce Solution 1;

(b). adding to Solution 1 a filler, preferably maltodextrin, an ester containing derivative of an acrylic polymer, preferably sodium polyacrylate and an anti-collapsing agent, preferably diglycine, to produce Solution 2;

(c). freezing Solution 2; and (f). lyophilizing the frozen Solution 2.

Step (b) may further include adding a taste-masking agent, preferably HPβCD complex, to produce Solution 2;

There is provided for pharmaceutical dosage forms in accordance with first and/or second aspect of this invention substantially as herein described, exemplified and/or illustrated with reference to any one of Examples 1 to 2 and the accompanying figures.

There is provided for a compound of Formula (I) substantially as herein described, exemplified and/or illustrated with reference to any one of Examples 1 to 2 and the accompanying figures.

There is provided for methods in accordance with any one of the fourth to sixth aspects of this invention substantially as herein described, exemplified and/or illustrated with reference to any one of Examples 1 to 2 and the accompanying figures.

BRIEF DESCRIPTION OF THE DRAWINGS

The invention is now described, by way of example only, with reference to the accompanying diagrammatic drawings, in which

FIG. 19 shows typical force-distance and force-time profiles of the wafer matrix of Formulation 1 (a drug-free embodiment of the second aspect of the invention) at distance mode for determining (a) matrix hardness (determined from gradient between anchors 1 and 2) and deformation energy (determined from AUC between anchors 1 and 2); and (b) matrix resilience;

FIG. 20 shows typical force-distance and force-time profiles of the wafer matrix of Formulation 1 (a drug-free embodiment of the second aspect of the invention) at strain mode for determining (a) matrix hardness (determined from gradient between anchors 1 and 2) and deformation energy (determined from AUC between anchors 1 and 2); and (b) matrix resilience;

FIG. 21 shows typical force-distance and force-time profiles of the wafer matrix of Formulation 1 (a drug-free embodiment of the second aspect of the invention) at force mode for determining (a) matrix hardness (determined from gradient between anchors 1 and 2) and deformation energy (determined from AUC between anchors 1 and 2); and (b) matrix resilience; and FIG. 22 shows a Linear isothermic plot, Log isothermic plot, linear BJH adsorption dV/dD curve for pore volume, and log BJH adsorption dV/dD curve for pore volume of the composite polymeric matrices of Formulation 1 (a drug-free embodiment of the second aspect of the invention). The figures confirm the presence of a "H4 hysteresis" of the isotherm.

DETAILED DESCRIPTION OF THE INVENTION

Figure 1:
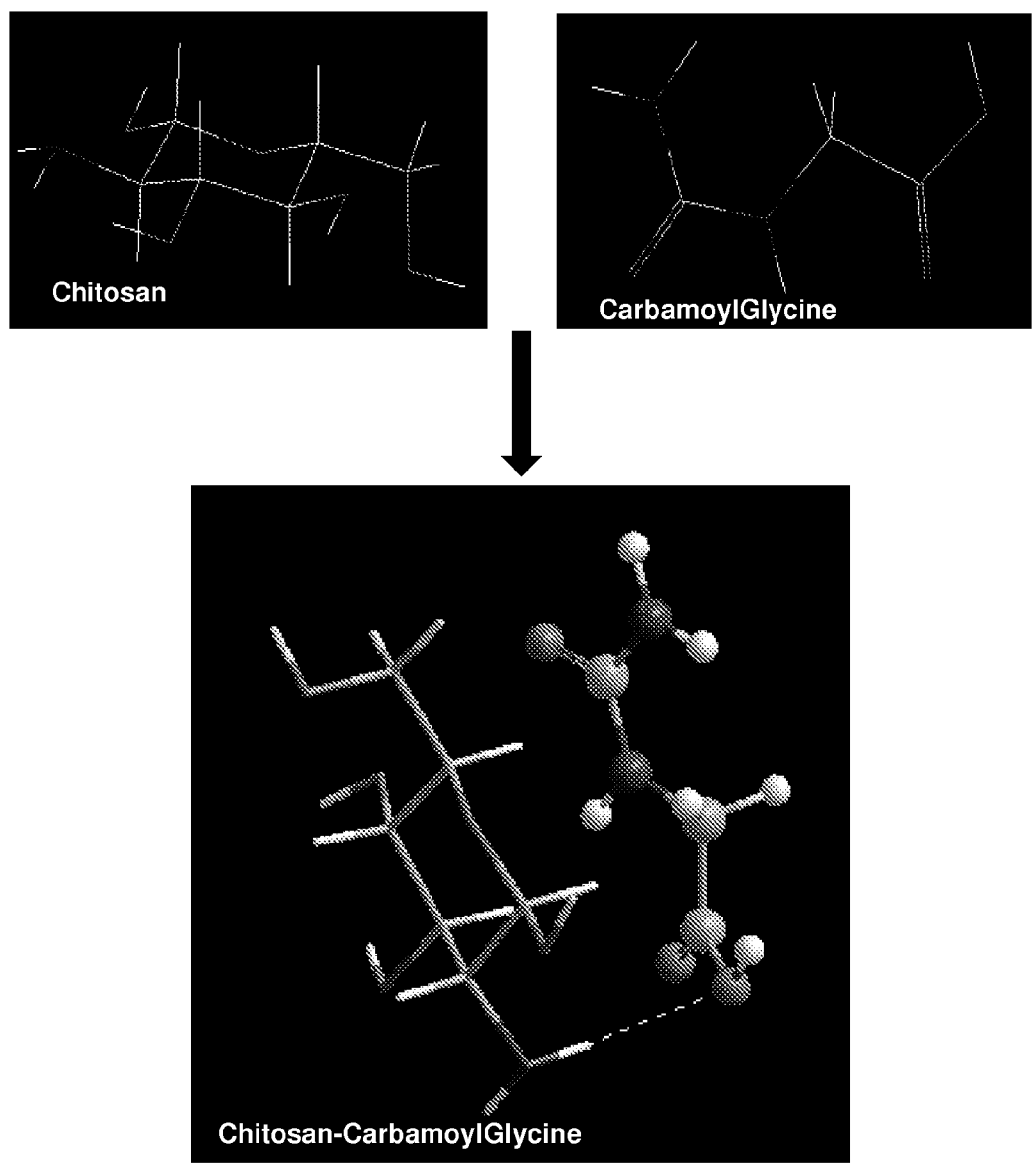
FIG. 1 shows a schematic representation of synthesis of chitosan carbamoyl glycine derivative via —NH$_2$—COOH— hydrogen bond formation as elucidated using molecular modelling simulations.

According to a first aspect of the invention there is provided a pharmaceutical dosage form for the release of at least one active pharmaceutical ingredient (API) at a target site in a human or animal, the pharmaceutical dosage form comprising a compound of the Formula (I):

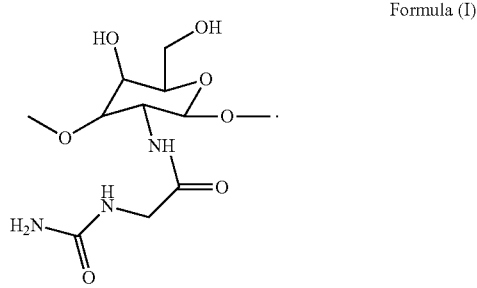

Formula (I)

The compound of the Formula (I) is a soluble ester chitosan derivative polymer and is herein termed carbomoyl glycinated chitosan (CmGC). The pharmaceutical dosage form may further comprise a soluble matrix forming polymer. Typically, the dosage form is used as an oral pharmaceutical dosage form, and more typically is formed into a wafer for abutment, in use, against mucosa in the oral cavity of a human and/or an animal. The term 'wafer' in this specification refers to a solid, laminar and rigid structure. The target site is typically the oral cavity of a human and/or animal. The dosage form may also be formed into a tablet, capsule and/or ocular dosage form. The ocular dosage form being a mini-tablet essentially comprising a solid eye drop.

Preferred embodiments of the dosage form according to the invention will be described below.

It is important to understand that the pharmaceutical dosage form according to this invention may be formulated as an oral wafer matrix, a graft lubricant, a chromatography gel, a wound dressing, a mesh, a degradable bone fixation glue, a degradable ligament glue and sealant, a tendon implant, a dental implant, a reconstituted nerve injectable, a disposable article, a disposable contact lens, an ocular device, a rupture net, a rupture mesh, an instant blood bag additive, an instant haemodialysis additive, an instant peritoneal dialysis additive, an instant plasmapheresis additive, an inhalation drug delivery device, a cardiac assist device, a tissue replacing implant, a drug delivery device, an endotracheal tube lubricant, a drain additive, and a dispersible suspension system.

It is to be understood that the dosage form according to the invention, especially in regard to a watered dosage form, incorporates advantages including the fact that no coating or microencapsulation is involved; there is a one-step formulation; no effervescence in use; robust and non-friable formulation (for geriatrics); no moisture sensitivity; no chewing required; no water insoluble content; no grittiness; and no remnants during and/or after use.

The dosage form according to the invention dissolves rapidly in aqueous media, especially when it comes into contact with the mucosal membranes of the mouth cavity in a human or animal. The rapid, and in fact, ultrafast disintegration, follows the following principle: the phenomenon involved in the fast disintegration of the dosage form, especially the wafers, is based on the use of freely water soluble polymeric/excipient blends. The important aspect for choosing the polymers/excipients is that the polymers/excipients should be soluble at physiological temperature (37° C.) without the aid of heating or stirring. The inherent individual solubility of the components is synergistically enhanced when used with other polymers/excipients in a particular ratio. The component with the highest solubility (maltodextrin in the preferred embodiment described herein below) was chosen as the bulk and hydroxypropyl cellulose was chosen for the matrix stability. Hydroxypropyl cellulose can be combined with a soluble novel derivative of chitosan namely carbamoyl glycinated chitosan (CmGC). This novel polymer is also easily dispersible in deionised water in lyophilized form and is capable of forming channels making the aqueous media to intrude rapidly. Being a polymeric ester, sodium polyacrylate was used to assist in rapid wettability and hence disintegration and solubility. Diglycine conferred microhardness properties at very low concentrations and provide required functional groups for hydrogen bonding rendering intactness to the wafer matrix dosage form. The combination of compounds comprising the wafer dosage forms in accordance with the invention involved a considerable amount of research and development. The very rapid dissolution characteristics and robust nature of the dosage forms of the first and second aspect of the invention could not have been predicted, are surprising and are advantageous when compared to the current state of the art.

The soluble matrix forming polymer may be at least one natural and/or synthetic polymer and may be selected from the group, but not limited to: polyanionic polysaccharides, carboxymethyl cellulose, carboxymethyl amylose, chondroitin-6-sulfate, dermatin sulfate, heparin, heparin sulfate, collagen, fibrinogen, albumin, fibrin, chitosan, hyaluronic acid, polyvinylpyrrolidone, polyvinyl alcohol) and its derivatives, poly(ethylene glycol) and its derivatives, pluronics, poloxamers, tetronics, polybutylene oxide, poly(ethylene oxide), polypropylene oxide), poly(ethylene oxide)-poly (propylene oxide)-poly(ethylene oxide), polyvinyl acetate), polyvinyl amine), pectin, carrageenan, dextran sulfate, polylysine, gelatin, carboxymethyl chitin, dextran, agarose, and pullulan.

In a preferred embodiment of the invention, the soluble matrix forming polymer is a starch derivative, in particular a hydroxyalkylated starch derivative, and specifically, hydroxypropyl cellulose.

The pharmaceutical dosage form may further comprise at least one ester containing derivative of an acrylic polymer selected from the group including, but not limited to: poly (hydroxyethyl methylacrylate), hydroxypropyl methacrylamide-based copolymers, polyacrylamide, poly(methacrylic acid-grafted-ethylene glycol), poly(N-2-hydroxypropyl methacrylamide), poly(2-hydroxyethylmethacrylate), poly (acrylic acid), poly-acrylamide, polyacrylonitrile, polycaprolactone, poly(ethylene imine), poly(ethyl methacrylate), propylene fumarate, poly(glucosylethyl methacrylate), poly (hydroxy butyrate), poly(hydroxyethyl methacrylate), poly (hydroxypropyl methacrylamide), and poly(methyl methacrylate) and their polyesters.

In a preferred embodiment of the invention, the ester containing derivative of an acrylic polymer is sodium polyacrylate.

The pharmaceutical dosage form may further comprise an anti-collapsing agent. The anti-collapsing agent may comprise an amino acid chain, preferably the amino acid chain having 1 amino acid residue, more preferably 2 amino acid residues. In a preferred embodiment of the invention, the anti-collapsing agent comprises an amino acid chain having two amino acid residues, preferably diglycine.

The pharmaceutical dosage form may further comprise a filler substance, in use binding and/or combining the various components comprising the dosage form, the filler substance may be at least one compound selected from the group including, but not limited to: maltodextrin (MD); dextrin; alkaline-modified starch; bleached starch; oxidized starch, enzyme-treated starch such as maltodextrin, cyclodextrin, monostarch phosphate, distarch phosphate by esterification, crosslinked starch, acetylated starch, hydroxypropylated starch, hydroxyethyl starch, cationic starch, carboxymethylated starch, phosphated distarch phosphate, hydroxypropyl distarch phosphate, acetylated oxidized starch. In a preferred embodiment of the invention, the starch derivative comprises an enzyme treated/hydrolyzed starch, more preferably maltodextrin.

The pharmaceutical dosage form may further comprise a taste masking agent, in use to mask the unsavoury taste of the dosage form, the taste masking agent may be at least one compound selected from the group including, but not limited to: macrocyclic compound such as but not limited to a cyclodextrins and their derivatives, porphyrins, ion exchange resins, cucurbiturils, permeation enhancing agents well known in the art such as surfactants (fatty acid derivatives—sodium decanoate), and stabilizers. In a preferred embodiment of the invention, the cyclodextrin derivative comprises a rapidly soluble derivative, more preferably hydroxypropyl-beta-cyclodextrin. It is to be understood that the taste masking agent may also act in use as a permeation enhancer.

The pharmaceutical dosage form may further comprise an active pharmaceutical ingredient (API). The API may be selected from the group including, but not limited to: smoking cessation drugs, narcotic analgesics, anesthetics, antitussives, normarcotic analgesics such as the nonsteroidal anti-inflammatory agents (NSAIDS), erectile dysfunction drugs, female sexual dysfunction drugs, antihistamines, cold and allergy drugs, drugs that combat cough, drugs that combat respiratory disorders, drugs that combat sore throat, drugs that combat heartburn and/or dyspepsia, antiemetics, sleep aids, drugs that combat diarrhea, drugs that improve oral hygiene, antagonists of CGRP receptors, drugs associated with migrane treatment, drugs for hormone replacement, drugs that combat Alzheimer's disease, sitagliptin, caffeine and caffeine salt compounds.

The API may be incorporated together with at least one of the soluble chitosan derivative polymer and/or the ester containing derivative of the acrylic acid and/or the anti-collapsing agent and/or the filler substance and/or the taste masking agent. API incorporation may take place via at least one of the group, but not limited to: non-covalent interactions, covalent interactions, van der Waals forces, electrostatic interactions and hydrogen bonding. The active pharmaceutical ingredient (API) may be incorporated within the taste masking agent hydroxypropyl-beta-cyclodextrin (HPβCD) to form a HPβCD-API inclusion complex.

An embodiment of the first aspect of the invention may be formulated as a placebo and lacking an API. Such a placebo embodiment may comprise: a compound of Formula (I), (carbamoyl glycinated-chitosan); a soluble matrix forming polymer, preferably hydroxypropyl cellulose (HPC); an ester containing derivative of an acrylic polymer, sodium polyacrylate; an anti-collapsing agent, preferably diglycine; and a filler substance, preferably maltodextrin.

The placebo according to the first aspect of the invention may additionally comprise a taste masking agent.

In a preferred embodiment of the first aspect of the invention the pharmaceutical dosage form may comprise: a compound of Formula (I), (carbamoyl glycinated-chitosan); a soluble matrix forming polymer, preferably hydroxypropyl cellulose (HPC); an ester containing derivative of an acrylic polymer, preferably sodium polyacrylate; an anti-collapsing agent, preferably diglycine; a filler substance, preferably maltodextrin; and a taste masking agent and API, preferably HPβCD-API inclusion complex.

According to a second aspect of the invention there is provided a pharmaceutical dosage form for the release of at least one active pharmaceutical ingredient (API) at a target site in a human or animal, the pharmaceutical dosage form comprising a soluble matrix forming polymer, an ester containing derivative of an acrylic polymer, an anti-collapsing agent, and a filler.

The pharmaceutical dosage form according to the second aspect of the invention, wherein the soluble matrix forming polymer may be of the class of cellulosic polymers, preferable hydroxypropyl cellulose, wherein the ester containing derivative of an acrylic polymer may be sodium polyacrylate, wherein the anti-collapsing agent may be diglycine, and wherein the filler substance may by maltodextrin.

Essentially, the second aspect of the invention is formulated without the use of the compound of Formula (I). In all other respects the alternative embodiment may be formulated to have the same chemical, physico-chemical and mechanical characteristics.

The second aspect of the invention may further comprise at least one active pharmaceutical compound (API). The second aspect may further comprise a taste masking agent. The second aspect of the invention may further comprise a taste masking agent and API, preferably hydroxypropyl-beta-cyclodextrin HPβCD-active pharmaceutical ingredient (API) inclusion complex (HPβCD-API inclusion complex).

It is to be understood that an embodiment of the second aspects of the invention may be formulated as a placebo and lacking an API. Such a placebo embodiment may comprise a soluble matrix forming polymer, preferably hydroxypropyl cellulose (HPC); an ester containing derivative of an acrylic polymer, preferably sodium polyacrylate; an anti-collapsing agent, preferably diglycine; and a filler substance, preferably maltodextrin.

The placebo according to the second aspect of the invention may additionally comprise a taste masking agent.

In a preferred embodiment of the second aspect of the invention the pharmaceutical dosage form may comprise a soluble matrix forming polymer, preferably hydroxypropyl cellulose (HPC); an ester containing derivative of an acrylic polymer, preferably sodium polyacrylate; an anti-collapsing agent, preferably diglycine; a filler substance, preferably maltodextrin; and a taste masking agent and API, preferably HPβCD-API inclusion complex.

It is to be understood that the dosage forms according to this invention may be homogenous, alternatively layered like a sandwich, alternatively layered like an onion. In the event that the dosage form is layered, each layer may include at least one of the same or different API.

According to a third aspect of the invention there is provided a compound of the Formula (I):

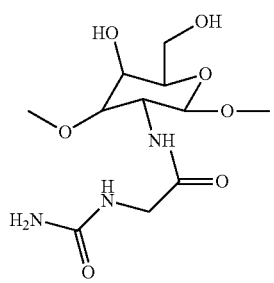

Formula (I)

It is to be understood that the compound may be polymeric in nature and that the compound is formed by the interaction of the carboxylic functionality (—COOH) of hydantoic acid with the amine functionality (—$NH_2$) of chitosan providing a stable novel polymer, namely carbamoyl glycinated chitosan. The bonding of carbamoyl glycinated chitosan is shown in FIG. 1 below.

According to a fourth aspect of the invention there is provided a method of manufacturing the compound of Formula (I) of the third aspect of this invention, herein termed carbamoyl glycinated chitosan, the method comprising the steps of:
(a). dissolving chitosan in a hydantoic acid solution;
(b). dialyzing said solution;
(c). freezing said dialyzed solution; and
(d). lyophilizing the frozen solution.

The method of manufacturing the compound of Formula (I) typically takes place via the following reaction:

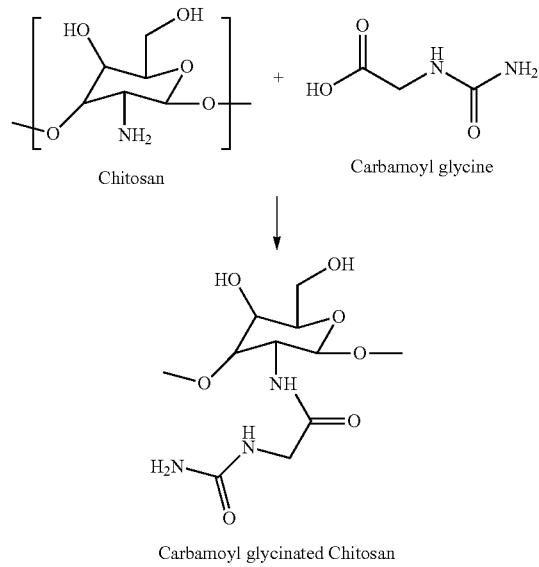

The above method is further explained in detail below.

According to a fifth aspect of the invention there is provided a method of manufacturing the pharmaceutical dosage form of the first aspect of this invention, the method comprising the steps of:

(a). dissolving a soluble matrix forming polymer, preferably hydroxy propyl cellulose (HPC), in a liquid medium, preferably deionized water to produce Solution 1;
(b). adding to Solution 1 a soluble chitosan derivative polymer, preferably the carbamoyl glycinated chitosan of the first aspect of the invention, to produce Solution 2;
(c). adding to Solution 2 a filler, preferably maltodextrin, an ester containing derivative of an acrylic polymer, preferably sodium polyacrylate and an anti-collapsing agent, preferably diglycine, to produce Solution 3;
(d). adding to Solution 3 a taste-masking agent, preferably HPβCD-API inclusion complex, to produce Solution 4;
(e). freezing Solution 4; and
(f). lyophilizing the frozen Solution 4.

Figure 11:
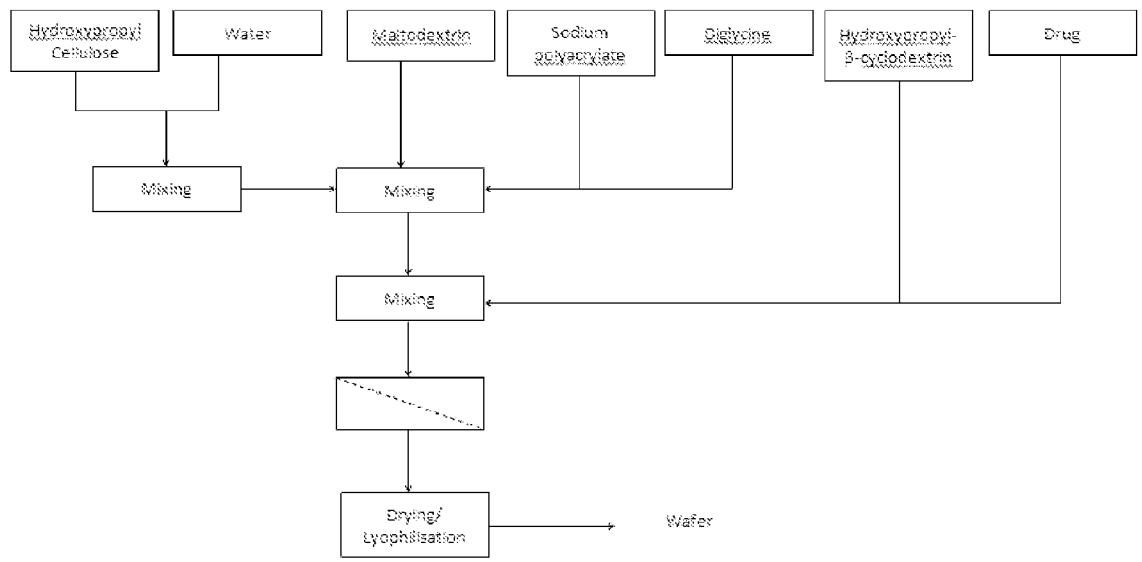
FIG. 11 shows a block flow diagram representing a method of manufacturing the dosage form of Wafer 2 in accordance with the second aspect of the invention (drug-free embodiment)

FIG. 11 shows a block flow diagram representing a method of manufacturing the dosage form according to the invention and illustrates and/or exemplifies the method according to this invention when read together with the Examples below.

According to a sixth aspect of the invention there is provided a method of manufacturing the pharmaceutical dosage form of the second aspect of this invention, the method comprising the steps of:
(a). dissolving a soluble matrix forming polymer, preferably hydroxy propyl cellulose (HPC), in a liquid medium, preferably deionized water to produce Solution 1;
(b). adding to Solution 1 a filler, preferably maltodextrin, an ester containing derivative of an acrylic polymer, preferably sodium polyacrylate and an anti-collapsing agent, preferably diglycine, to produce Solution 2;
(c). freezing Solution 2; and
(f). lyophilizing the frozen Solution 2.

Step (b) may further include adding a taste-masking agent, preferably HPβCD complex, to produce Solution 2;

Example 2 below, particularly describes and/or illustrates and/or exemplifies the method of manufacturing the dosage form according to the second aspect of the invention.

It is to be understood that the unique combination of components that comprise the dosage form according to the preferred embodiment of the second aspect of the invention imparts very specific three dimensional architecture to the solid dosage form. These components are the soluble matrix forming polymer (preferably HPC), the ester containing derivative of an acrylic polymer (preferably sodium polyacrylate), an anti-collapsing agent (preferably diglycine), and a filler substance (preferably maltodextrin). The SEM figures show aligned laminar troughs or channels that lead into the interior of the dosage form. These troughs or channels allow for the rapid ingress of fluid in use causing rapid disintegration and/or dissolution. The combination of components impart this physico-mechanical property to the dosage form. The XRD shows that diglycine improves crystallinity to the overall structure which is balanced by other more amorphous components. The formation of the troughs or channels seen on the SEM figures also imparts increased stability and rigidity to the dosage form. The formation of the troughs and/or channels in the three dimensional structure is surprising and unexpected.

Representative examples of the invention are described in detail hereunder.

Example 1

Wafer 1

In a preferred embodiment of the first aspect of the invention the pharmaceutical dosage form was manufactured to be a multi-constituent system displaying, in use, rapid disintegration, the dosage form being formed into a wafer and comprising:
  i. a soluble chitosan derivative polymer, preferably carbamoyl glycinated-chitosan (CmGC)
  ii. a soluble matrix forming polymer, preferably hydroxypropyl cellulose (HPC);
  iii. an ester containing derivative of an acrylic polymer, preferably sodium polyacrylate;
  iv. an anti-collapsing agent, preferably diglycine;
  v. a filler substance, preferably maltodextrin; and
  vi. a taste masking agent and API, preferably hydroxypropyl-beta-cyclodextrin HPβCD-active pharmaceutical ingredient (API) inclusion complex (HPβCD-API inclusion complex).

A placebo may also be manufactured by simply excluding item (vi) above during the manufacturing process. However, it is to be understood that placebos may include a taste masking agent without API.

When the term 'rapid disintegration' or 'rapid dissolution' is used in this specification it means fast ingress of fluid into a dosage form and immediate onset of dissolution and/or disintegration of the dosage form.

Methods
Preparation of Carbamoyl Glycinated Chitosan (CmGC) (According to a Third Aspect of the Invention)

Chitosan (2 g) was dissolved in 50 mL of 2% w/v hydantoic acid solution until a clear solution is obtained. The resulting solution was centrifuged to remove any particulate matter. The supernatant from the centrifuged solution was then dialyzed (cellulose membrane; MWCO 12,000 Da) against 1000 mL of deionized water for 48 hours with replenishment of deionized water every 6 hours. The dialyzed solution so obtained was frozen at −82° C. for 12 hours followed by lyophilization at 25 mtorr/−42° C./12 hours (FreeZone® 2.5, Labconco®, Kansas City, Mo., USA). The lyophilized sample was pulverized and stored for further use in a desiccator.

Preparation of the Hydroxypropyl-β-Cyclodextrin-Active Pharmaceutical Ingredient (API) (HPβCD-API) Complex A specified amount of API and HPβCD (in a specified ratio to the API) were dissolved in a common solvent (in which both the API and HPβCD were soluble), preferably deionized water, until clear solutions were obtained, preferably at the saturation solubility of the API. The resulting HPβCD-API inclusion complex solution so obtained was frozen at −82° C.

TABLE 1

Dosage form components of the pharmaceutical dosage form according to the first aspect of the invention, and their specific function(s) (Wafer 1 - drug-free placebo embodiment)

| S. No. | Component | Compound | Function(s) |
|---|---|---|---|
| 1. | Soluble chitosan derivative polymer | Carbamoylglycinated-chitosan | Rapidly soluble polymer; unique soluble polymeric ester providing the fibrous matrix for rapid water channeling and directional flow |
| 2. | Soluble matrix forming agent | Hydroxypropyl cellulose | Soluble polymer; robust matrix forming polymer |
| 3. | Ester containing derivative of an acrylic polymer | Ester containing derivative of sodium polyacrylate | Soluble polymer; ester components for initiation of rapid solubility |
| 3. | Filler substance | Maltodextrin | soluble bulk filler component; cryoprotectant |
| 5. | Anti-collapsing agent | Diglycine | Microhardness providing agent and/or prevents collapse of dosage form |
| 6. | Taste masking agent | Hydroxypropyl-β-cyclodextrin (HPβCD) | Solubilizing agent, permeation enhancer, and taste masking agent |

Preferred embodiments of the dosage forms were prepared as watered pharmaceutical dosage forms, where a wafer is a solid, laminar, rigid structure. Preparatory methods describing the manufacture and/or preparation of the various components of the watered dosage form and/or the watered dosage form itself, will now be described in detail. Characterization experiments of the various components of the watered dosage form and/or of the watered dosage form itself will also be discussed.

Materials
Chitosan (low molecular weight, Sigma-Aldrich, St. Louis, Mo., USA, Lot#MKBF2754V); hydantoic acid (N-Carbomoylglycine, Sigma-Aldrich, St. Louis, Mo., USA)]; Hydroxypropyl cellulose (KLUCEL®, Type: EF, Hercules Incorporated, Wilminton, Del., USA); Maltodextrin (Dextrose equivalent 16.5-19.5, Sigma-Aldrich, St. Louis, Mo., USA); Sodium Polyacrylate (average $M_w$~2100 Da, Sigma-Aldrich, St. Louis, Mo., USA); Diglycine (Gly-Gly, Sigma-Aldrich, St. Louis, Mo., USA); Hydroxypropyl-β-Cyclodextrin (average $M_w$~1,460, Sigma-Aldrich, St. Louis, Mo., USA).

for 12 hours followed by lyophilization at 25 mtorr/−42° C./12 hours (FreeZone® 2.5, Labconco®, Kansas City, Mo., USA) to yield the drug—HPβCD inclusion complex. The lyophilized sample was pulverized and stored for further use in a desiccator. Should lyophilization not be used, micronisation may be used, especially in embodiments of the invention where inhaler or spray dosage forms are to be manufactured.

Preparation of the Pharmaceutical Dosage Form (According to an Embodiment of the First Aspect of the Invention):

A specified quantity of hydroxypropyl cellulose (HPC) was dissolved in deionized water to make a clear solution 1. To solution 1, carbamoyl glycinated chitosan was added and allowed to dissolve completely to obtain solution 2. Thereafter, specified quantities of maltodextrin, sodium polyacrylate, and diglycine were added to solution 2 and stirred to complete solubilisation to form solution 3. A specified quantity of HPβCD-API inclusion complex was added to solution 3 as the last addition to obtain solution 4. The solution 4 obtained above was filtered to remove any particulate matter and was poured into circular moulds of various capacities such as 0.25 cc; 0.4 cc; and 0.75 cc. The moulds were then frozen at −82° C. for 12 hours followed by lyophilization at 25 mtorr/−42° C./5 hours to obtain the final dosage form. The final dosage forms were wafers. It is to be understood that the API may be incorporated into the dosage using various means and need not necessarily be incorporated therewith through the use of the HPβCD-API inclusion complex. Should lyophilization not be used, micronisation may be used, especially in embodiments of the invention where inhaler or spray dosage forms are to be manufactured.

Placebo wafers according to both the first and second aspect of the invention were manufactured according to Tables 2 and 3 below.

TABLE 2

Wafer 2- Placebo wafer matrix (an embodiment of the second aspect of the invention)

| | |
|---|---|
| Hydroxypropyl cellulose | 0.5% w/v |
| Maltodextrin | 5.0% w/v |
| Sodium Polyacrylate | 0.25% w/v |
| Diglycine | 0.25% w/v |
| Hydroxypropyl-β-Cyclodextrin | 1.0% w/v |

TABLE 3

Wafer 1- Placebo wafer matrix (an embodiment of the first aspect of the invention)

| | |
|---|---|
| Hydroxypropyl cellulose | 0.5% w/v |
| carbamoyl glycinated chitosan | 0.5% w/v |
| Maltodextrin | 5.0% w/v |
| Sodium Polyacrylate | 0.25% w/v |
| Diglycine | 0.25% w/v |
| Hydroxypropyl-β-Cyclodextrin | 1.0% w/v |

Results and Discussion:

Synthesis of Carbamoyl Glycinated Chitosan (CmGC) for Wafer 1:

Carbamoyl glycinated chitosan (CmGC) or chitosan-hydantoate is a novel chitosan derivative having the characteristic property in being rapidly soluble in deionized water without requiring acidic conditions. The derivative is formed by the interaction of the carboxylic functionality (—COOH) of hydantoic acid with the amine functionality (—$NH_2$) of chitosan as shown below and discussed further in detail in the FTIR description below. Notably, the —COOH/—$NH_2$ interaction in case of carbamoyl glycinated chitosan differs from that of acetic acid-chitosan and citric acid-chitosan. This is evident from the fact that acetic acid-chitosan is not soluble in deionized water after lyophilisation. In case of citric acid-chitosan; chitosan precipitates out during the dialysis stage because of diffusion of citric acid from the mixture leaving the chitosan insoluble again. This confirms that carbamoyl glycinated chitosan forms a very stable bond by simple mixing and requires no special reactants for the —COOH/—$NH_2$ interaction. FIG. 1 shows a schematic representation of synthesis of chitosan carbamoyl glycine derivative via —$NH_2$—COOH— hydrogen bond formation as elucidated using molecular modelling simulations. The —COOH group of carbamoylglycine can be conjugated to the —$NH_2$ group of chitosan by carobodiimide chemistry or any other type of chemistry known to a person skilled in the art of forming an amide bond.

Structural Characterization of Chitosan Carbamoyl Glycine Derivative (CmGC)

FTIR Analysis of Chitosan, Carbamoyl Glycine and Chitosan Carbamoyl Glycine Derivative for Wafer 1

Figure 2:
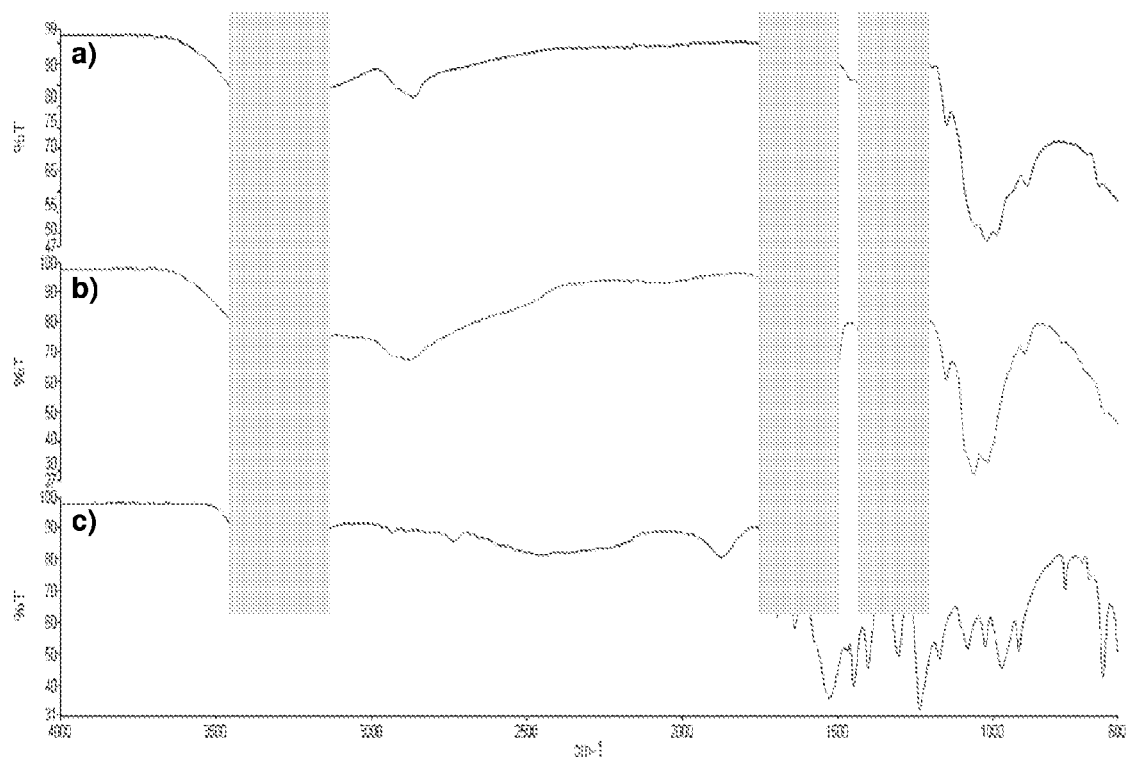
FIG. 2 shows Fourier transform infra-red spectra of (a) pristine chitosan; (b) carbamoyl glycinated chitosan (CmGC); and (c) pristine carbamoyl glycine.

Characteristic peaks assignment of chitosan (FIG. 2a) are: 3359 $cm^{-1}$ (O—H stretch overlapped with N—H stretch), 2868 $cm^{-1}$ (C—H stretch), 1640 $cm^{-1}$ (amide II band, C—O stretch of acetyl group), 1588 $cm^{-1}$ (amide II band, N—H stretch), 1485-1375 $cm^{-1}$ (asymmetric C—H bending of $CH_2$ group) and 1022 $cm^{-1}$ (bridge O stretch) of glucosamine residue. The IR spectral band of carbamoyl glycine showed characteristic peaks at (FIG. 2b): 3386 $cm^{-1}$, 3220 $cm^{-1}$, 2735 $cm^{-1}$, 2452 $cm^{-1}$, 1872 $cm^{-1}$, 1694 $cm^{-1}$, 1664 $cm^{-1}$, 1637 $cm^{-1}$, 1523 $cm^{-1}$, 1448 $cm^{-1}$, 1402 $cm^{-1}$, 1305 $cm^{-1}$, 1236 $cm^{-1}$, 1172 $cm^{-1}$, 1083 $cm^{-1}$, 1025 $cm^{-1}$, 972 $cm^{-1}$, 918 $cm^{-1}$, 768 $cm^{-1}$, 713 $cm^{-1}$, 647 $cm^{-1}$. FIG. 2c shows the significant peaks of chitosan carbamoyl glycine derivative. The peaks corresponding to chitosan are 2882 $cm^{-1}$, 1602 $cm^{-1}$, 1382 $cm^{-1}$, 1151 $cm^{-1}$, 1019 $cm^{-1}$ and 899 $cm^{-1}$. The new peak appearing 3262 $cm^{-1}$ (3386 $cm^{-1}$ and 3220 $cm^{-1}$ merge), 1518 $cm^{-1}$, 1382 $cm^{-1}$, 1304 $cm^{-1}$, and 1248 $cm^{-1}$ indicates the incorporation of the carbamoyl glycine moieties. The FTIR results suggest that the —COOH group of HA have been successfully bonded to the $NH_2$ group of chitosan main chain to form amide linkage. When viewing FIG. 2, FIG. 2 shows Fourier transform infra-red spectra of (a) pristine chitosan; (b) carbamoyl glycinated chitosan; and (c) pristine carbamoyl glycine.

Figure 5:
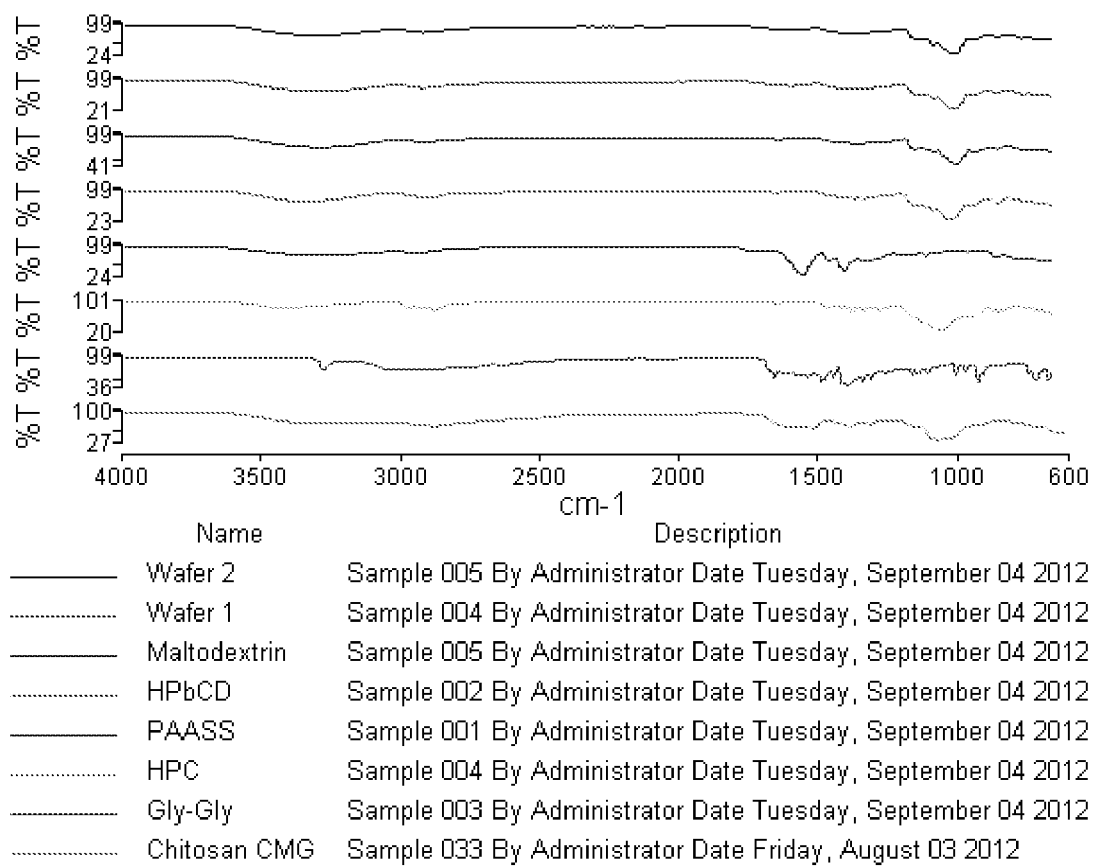
FIG. 5 shows Fourier transform infra-red spectra of the pharmaceutical dosage forms of Wafer 1 & 2 (drug-free embodiments of the first and second aspects of the invention respectively) and the inherent components of Wafer 1 thereof.

FTIR Spectral Analysis of the Placebo Wafer 1 (as Per Table 3):

The FTIR spectra of all the constituent components and the overall dosage form of Wafer 1 are depicted in FIG. 5. The FTIR spectra of the overall dosage form of Wafer 2 is also shown. A detailed analysis of the unique and general contribution of the components to the formation of final structure can be elucidates as shown in Table 4 and as discussed below.

It is evident from FTIR analysis that all the components are uniformly distributed in the dosage form irrespective of the concentration of the component as all the components contributed to the generation of transmittance spectra with maltodextrin forming the major part of the dosage form—the bulk filler.

The broad peak contribution of sodium polyacrylate (NaPAA) (3308 $cm^{-1}$) confirms its role as the ester polymer coating the granular matrix rather than being the inherent matrix itself. In this example embodiment of the invention the dosage form is not layered but there is provided that it may be formulated as sandwiched layered structures. The NaPAA is not a coating of the dosage form. The word "coating" is used to indicate that the NaPAA may be spread homogenously in the matrix in the form of a coating on the "microenvironment" of the wafer matrix making the dosage form rapidly disintegrating when in use.

The highly prominent band at 1373 $cm^{-1}$ arising from the CH bending vibration in cellulose confirmed the intact presence of the cellulosic structure and hence the robustness of the dosage form, in this case formed into a wafer, can be assured.

The presence of diglycine characteristic peak (—$CH_2$—$CH_2$—) in the finger print region (704 $cm^{-1}$) and also in the aliphatic region (2923 $cm^{-1}$) fulfils the hydrophobicity condition (among the all-hydrophillic system involved in lyophilization) required for the anti-collapsing micro-hardening property of diglycine in the final formulation.

The ubiquitous presence of hydroxyporpyl-β-cyclodextrin along the polymeric matrix encourages the fact that the drug will be uniformly dispersed once complexed with the cyclodextrin thereby providing adequate release. Given the short time of disintegration of the matrix, this might appear insignificant.

The incorporation of carbamoyl glycinated chitosan into the above formulation shifted the very intense 995 cm$^{-1}$ peak (Wafer 1) to 1013 cm$^{-1}$ peak corresponding to that of carbamoyl glycinated chitosan and hence proving the potential effect of incorporating this novel fibrous polymer to the matrix.

The shifting and change in intensity of various transmittance peaks along with the occurrence of a peak at 1590 cm$^{-1}$ confirms the formation of a unique blend having all the inherent functionalities of the components as well as a novel interaction profile of the components.

TABLE 4

FTIR spectral analysis of the Wafer 1 & 2, pharmaceutical dosage form, with respect to the component polymers

| S. No. | Wavelength Number for Wafer 2 (embodiment of the second aspect) | Corresponding wavelength number of the component(s) |
|---|---|---|
| 1. | 3308 cm$^{-1}$ | Sodium polyacrylate (3306 cm$^{-1}$) |
| 2. | 2922 cm$^{-1}$ | Diglycine (2923 cm$^{-1}$) Hydroxypropyl-β-Cyclodextrin (2925 cm$^{-1}$) Maltodextrin (2923 cm$^{-1}$) |
| 3. | 1590 cm$^{-1}$ | Unique to the wafer system |
| 4. | 1373 cm$^{-1}$ | Hydroxypropyl cellulose (1373 cm$^{-1}$) |
| 5. | 1148 cm$^{-1}$ | Hydroxypropyl-β-Cyclodextrin (1148 cm$^{-1}$) Maltodextrin (1147 cm$^{-1}$) |
| 6. | 1077 cm$^{-1}$ | Hydroxypropyl-β-Cyclodextrin (1079 cm$^{-1}$) Maltodextrin (1076 cm$^{-1}$) |
| 7. | 995 cm$^{-1}$ | Maltodextrin (991 cm$^{-1}$) |
| 8. | 930 cm$^{-1}$ | Maltodextrin (927 cm$^{-1}$) |
| 9. | 848 cm$^{-1}$ | Maltodextrin (847 cm$^{-1}$) Hydroxypropyl-β-Cyclodextrin (848 cm$^{-1}$) |
| 10. | 758 cm$^{-1}$ | Maltodextrin (758 cm$^{-1}$) Hydroxypropyl-β-cyclodextrin (755 cm$^{-1}$) |
| 11. | 704 cm$^{-1}$ | Diglycine (706 cm$^{-1}$) |
| | Wavelength Number shift for Wafer 1 (embodiment of the first aspect of the invention) | |
| 1. | 995 cm$^{-1}$ to 1013 cm$^{-1}$ | carbamoyl glycinated chitosan (1019 cm$^{-1}$) |
| 2. | 3308 cm$^{-1}$ | Sodium polyacrylate (3306 cm$^{-1}$) |
| 3. | 2922 cm$^{-1}$ | Diglycine (2923 cm$^{-1}$) Hydroxypropyl-β-Cyclodextrin (2925 cm$^{-1}$) Maltodextrin (2923 cm$^{-1}$) |
| 4. | 1590 cm$^{-1}$ | Unique to the wafer system |
| 5. | 1373 cm$^{-1}$ | Hydroxypropyl cellulose (1373 cm$^{-1}$) |
| 6. | 1148 cm$^{-1}$ | Hydroxypropyl-β-Cyclodextrin (1148 cm$^{-1}$) Maltodextrin (1147 cm$^{-1}$) |
| 7. | 1077 cm$^{-1}$ | Hydroxypropyl-β-Cyclodextrin (1079 cm$^{-1}$) Maltodextrin (1076 cm$^{-1}$) |
| 8. | 995 cm$^{-1}$ | Maltodextrin (991 cm$^{-1}$) |
| 9. | 930 cm$^{-1}$ | Maltodextrin (927 cm$^{-1}$) |
| 10. | 848 cm$^{-1}$ | Maltodextrin (847 cm$^{-1}$) Hydroxypropyl-β-Cyclodextrin (848 cm$^{-1}$) |
| 11. | 758 cm$^{-1}$ | Maltodextrin (758 cm$^{-1}$) Hydroxypropyl-β-cyclodextrin (755 cm$^{-1}$) |
| 12. | 704 cm$^{-1}$ | Diglycine (706 cm$^{-1}$) |

Differential Scanning Calorimetry (DSC) Analysis of Chitosan, Carbamoyl Glycine and Chitosan Carbamoyl Glycine Derivative (CmGC) for Wafer 1

Figure 3:
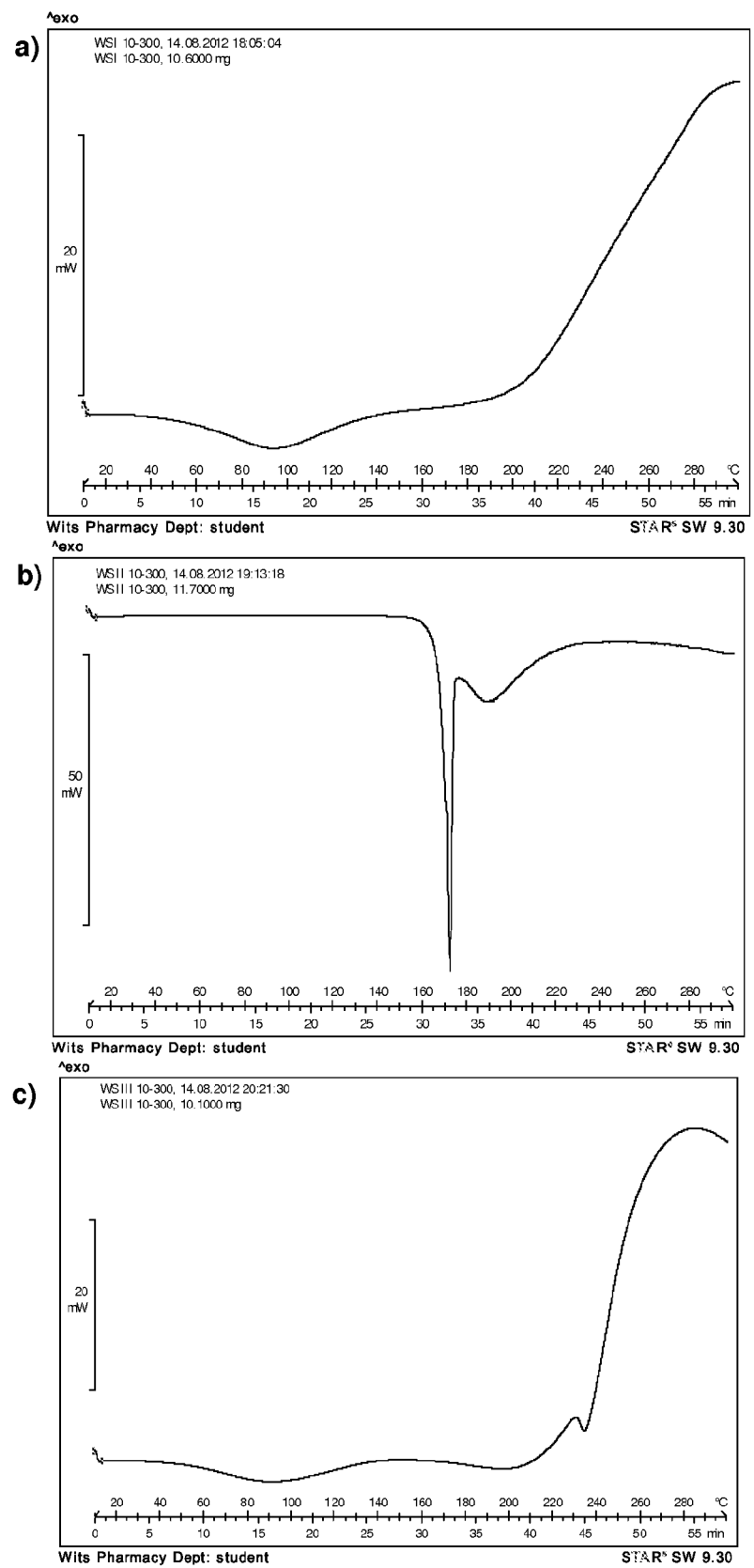
FIG. 3 shows differential scanning calorimetry (DSC) curves of (a) pristine chitosan; (b) pristine carbamoyl glycine; and (c) carbamoyl glycinated chitosan (CmGC)

FIG. 3 revealed differential scanning calorimetric analysis curves of pristine chitosan (FIG. 3a), pristine carbamoyl glycine (FIG. 3b) and chitosan carbamoyl glycine derivative (FIG. 3c). From the DSC curves, two endothermic stages appeared in the thermal analysis of chitosan. The first stage began at about 100° C. due to the loss of residual or physically adsorbed water, and the second stage showed an endothermic peak at 203° C. which corresponds to the Tg of chitosan (CHT). The DSC curve of hydantoic acid also showed two peaks at 172° C. (melting point of carbamoyl glycine) and 195° C. (decomposition peak). The chitosan carbamoyl glycine derivative however showed three major endothermic steps assigned by chitosan and the conjugated groups, individually. Different from the peak of chitosan at 203° C., a flat peak at 210° C. and a sharp peak at 236° C. were preset in chitosan derivative, which clearly revealed that the degradation peak temperature of chitosan derivative was higher than that of chitosan. Additionally, the sharp peak manifested that chitosan derivative degraded very fast at the temperature range close to 240° C., which resulted from a series of complex chemical changes in the process including the sugar ring dehydration, degradation, molecular chain glycine and N-deacetylation of the cracking unit, as well as the disruption of the ordered structure of chitosan by the introduction of the carbamoyl moeity. FIG. 3 shows differential scanning calorimetry curves of (a) pristine chitosan; (b) pristine carbamoyl glycine; and (c) carbamoyl glycinated chitosan.

X-Ray Diffraction (XRD) Analysis Chitosan, Carbamoyl Glycine and Chitosan-Carbamoyl Glycine Derivative (CmGC) for Wafer 1

Owing to the presence of the a) well-defined; b) uniformly-distributed, c) uni-directional, d) multi-lamellar, fibrous structure—the amorpho-crystal nature of the said polymer may play a significant role in providing the insight of the inherent mechanism of superior performance of the novel polymer. Apart from the structural and thermals analysis, preliminary XRD analysis shows a very unique amorphocrystalline profile and the final elucidation is under process.

Detailed XRD analysis is being carried out for the confirmation of the exact mechanism of this high-performance API delivery system. XRD analysis will provide the amorphocrystalline profile and the final elucidation is under process.

Morphology of Carbamoyl Glycinated Chitosan (CmGC) Wafer 1

Figure 4:
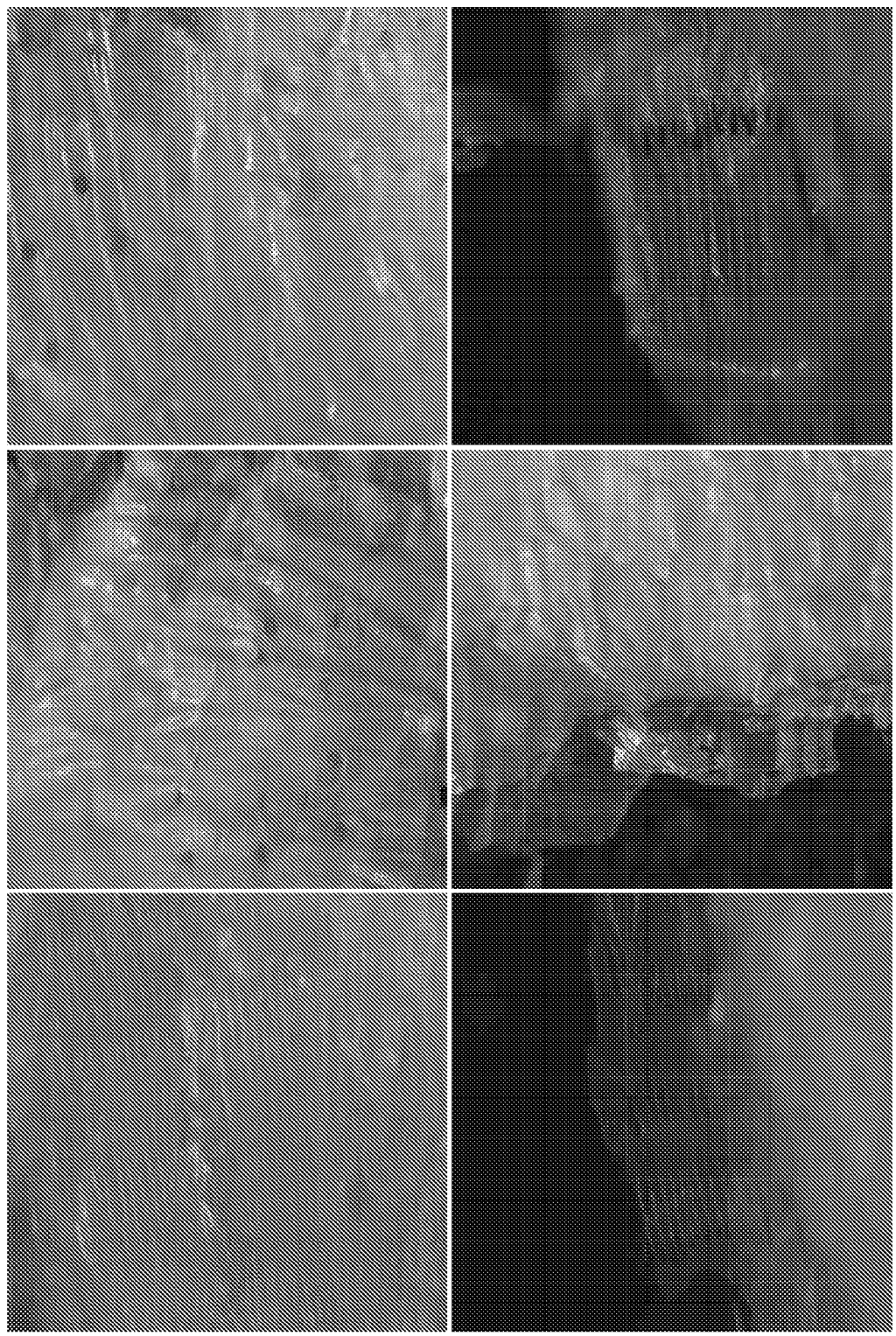
FIG. 4 shows photomicrographs of the lyophilized carbamoyl glycinated chitosan (CmGC) depicting the well-defined; uniformly-distributed; uni-directional; multi-lamellar; and fibrous structure.

The unique morphology of carbamoylglycinated-chitosan is depicted in FIG. 4. It is evident from the photomicrographs that the lyophilized form consists of a) well-defined; b) uniformly-distributed, c) uni-directional, d) multi-lamellar, fibrous structure which led to an instant ingress of aqueous phase making carbamoyl glycinated chitosan "an instantly soluble chitosan derivative". The parallel-channels formed during the lyophilisation phase rendered rapid influx of aqueous phase inside the polymer matrix leading to rapid disintegration and dissolution of the dosage form.

Morphology of the Developed Pharmaceutical Dosage Forms (Wafer 1)

Figure 6:
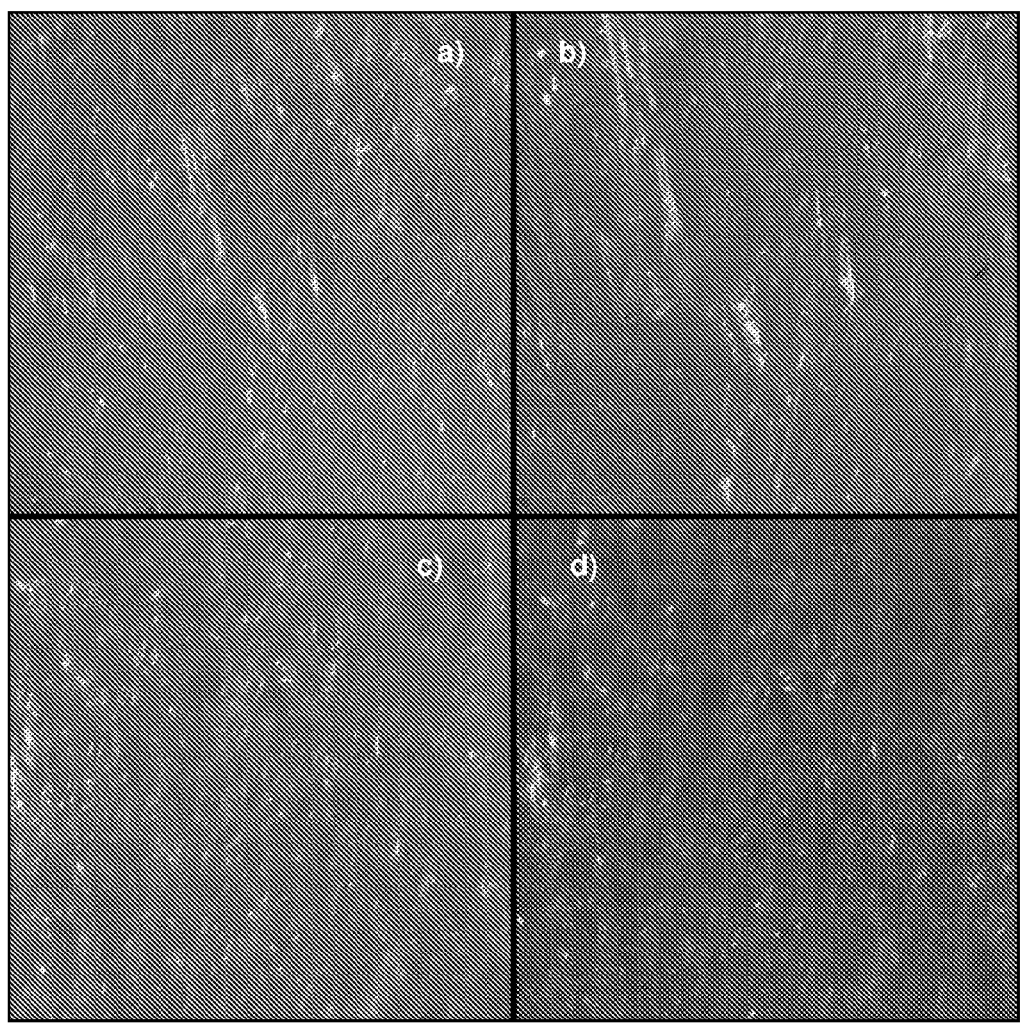
FIG. 6 shows photomicrographs showing a) and b) the surface of the wafer matrices; c) and d) the horizontal cross-sectional porous structure of Wafer 1 in accordance with the first aspect of the invention.
Figure 7:
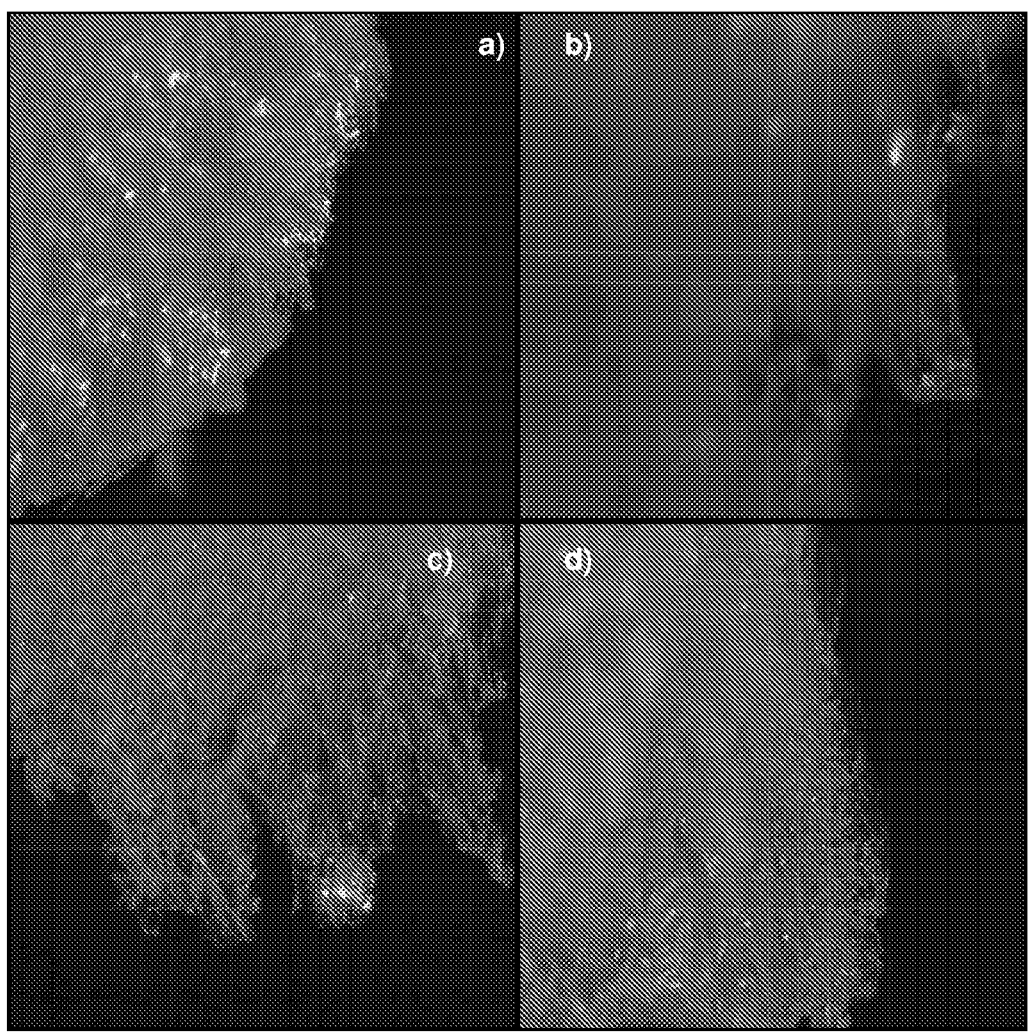
FIG. 7 shows photomicrographs showing a) and b) the layered structure vertically; c) and d) the connected fibrous structure of the watered pharmaceutical dosage form (vertical cross-section) of Wafer 1 in accordance with the first aspect of the invention.

As depicted in FIG. 6 and FIG. 7; it can be concluded that:

The upper surface of the watered dosage form (the surface from which the water phase escaped during lyophilization) was crystalline in appearance: the surface structure is likely to disperse amongst the constituents microcrystalline environment leading to separation of these parts as soon as the aqueous phase makes a contact with the wafer (FIG. 6a and FIG. 6b).

The horizontal cross-sectional area is highly porous with the pore size ranging from macro- to micropores: this continuous porous structure is likely to help in rapid ingress of aqueous phase leading to dispersion as well as dissolution of the matrix structure (FIG. 6c and FIG. 6d).

In order to take the photomicrographs of FIG. 7; the dosage form was broken to visualise the vertical cross-section. The dosage form appeared layered in nature: this layer-by-layer structure is likely to assist the aqueous phase to disperse the dosage form stage-by-stage leading to independent dispersion and dissolution of one layer with respect to other. This divides the dosage form into various microstructures to be acted upon by the ingress aqueous phase. Additionally, these independent microstructures will ensure the rapid disintegration of the dosage form independent of the size of the final formulation (FIGS. 7a and 7b).

FIGS. 7c and 7d display a micrograph inherent to a single layer in the dosage form's structure: the fibrous nature of the polymer composite can be visualized in the micrograph further explaining the robustness and connectivity of the matrix forming the dosage form. It is the unique combination of components comprising the Wafer 1 that allows for channels, typically parallel channels, to be formed. These channels facilitate rapid ingress of water and rapid disintegration and/or dissolution in use, and were surprising and expected physico-mechanical features of the Wafer 1. The three dimensional architecture is a function of the individual components of the Wafer 1 and also ensures sufficient rigidity to the wafer prior to use. Increased rigidity facilitates ease of use, since the dosage form will not disintegrate and/or break when handled by a user.

Figure 8:
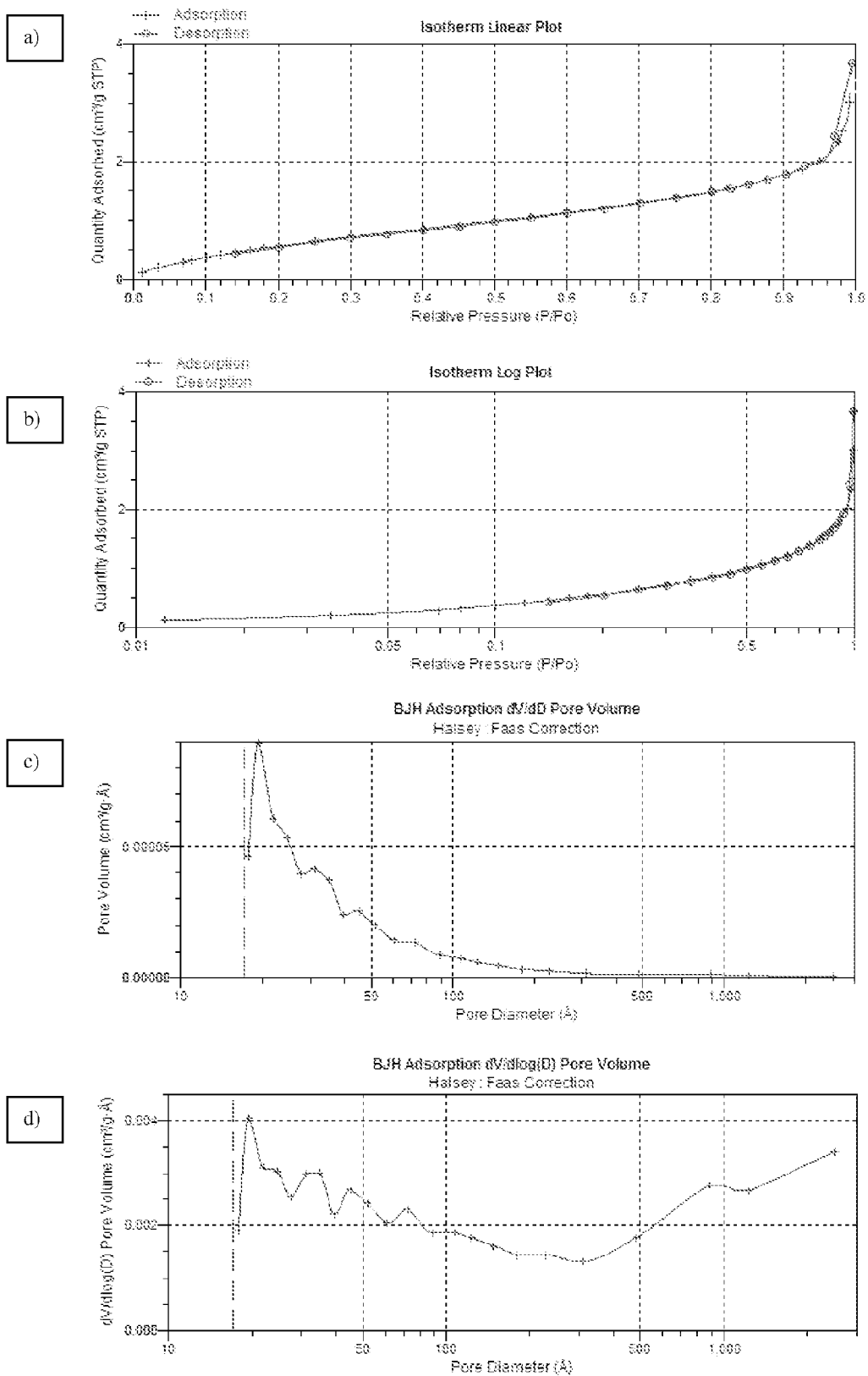
FIG. 8 shows a) a linear isothermic plot, b) a log isothermic plot, c) a linear BJH adsorption dV/dD curve for pore volume, and d) a log BJH adsorption dV/dD curve for pore volume of the composite polymeric matrices of Wafer 1 in accordance with the first aspect of the invention. The FIGS. 8 a-d confirm the presence of a "H4 hysteresis" of the isotherm.

| Porositometric quantification of the developed wafer dosage forms (Wafer 1) | |
|---|---|
| Surface Area | |
| Single point surface area at P/Po = 0.200637096: | 1.9615 m$^2$/g |
| BET Surface Area: | 2.6956 m$^2$/g |
| t-Plot External Surface Area: | 4.2946 m$^2$/g |
| BJH Adsorption cumulative surface area of pores between 17.000 Å and 3000.000 Å diameter: | 2.625 m$^2$/g |
| BJH Desorption cumulative surface area of pores between 17.000 Å and 3000.000 Å diameter: | 2.5504 m$^2$/g |
| FIG. 8 shows linear isothermic plot, log isothermic plot, linear BJH adsorption dV/dD curve for pore volume, and log BJH adsorption dV/dD curve for pore volume of the composite polymeric matrices. The figures confirm the presence of a "H4 hysteresis" of the isotherm. | |
| Pore Volume | |
| Single point adsorption total pore volume of pores less than 808.805 Å diameter at P/Po = 0.975468283: | 0.003604 cm$^3$/g |
| t-Plot micropore volume: | −0.000998 cm$^3$/g |
| BJH Adsorption cumulative volume of pores between 17.000 Å and 3000.000 Å diameter: | 0.005569 cm$^3$/g |
| BJH Desorption cumulative volume of pores between 17.000 Å and 3000.000 Å diameter: | 0.005528 cm$^3$/g |
| Pore Size | |
| Adsorption average pore width (4V/A by BET): | 53.4764 Å |
| BJH Adsorption average pore diameter (4V/A): | 84.867 Å |
| BJH Desorption average pore diameter (4V/A): | 86.694 Å |

Performance of the Pharmaceutical Dosage Form

TABLE 5

Figure 9:
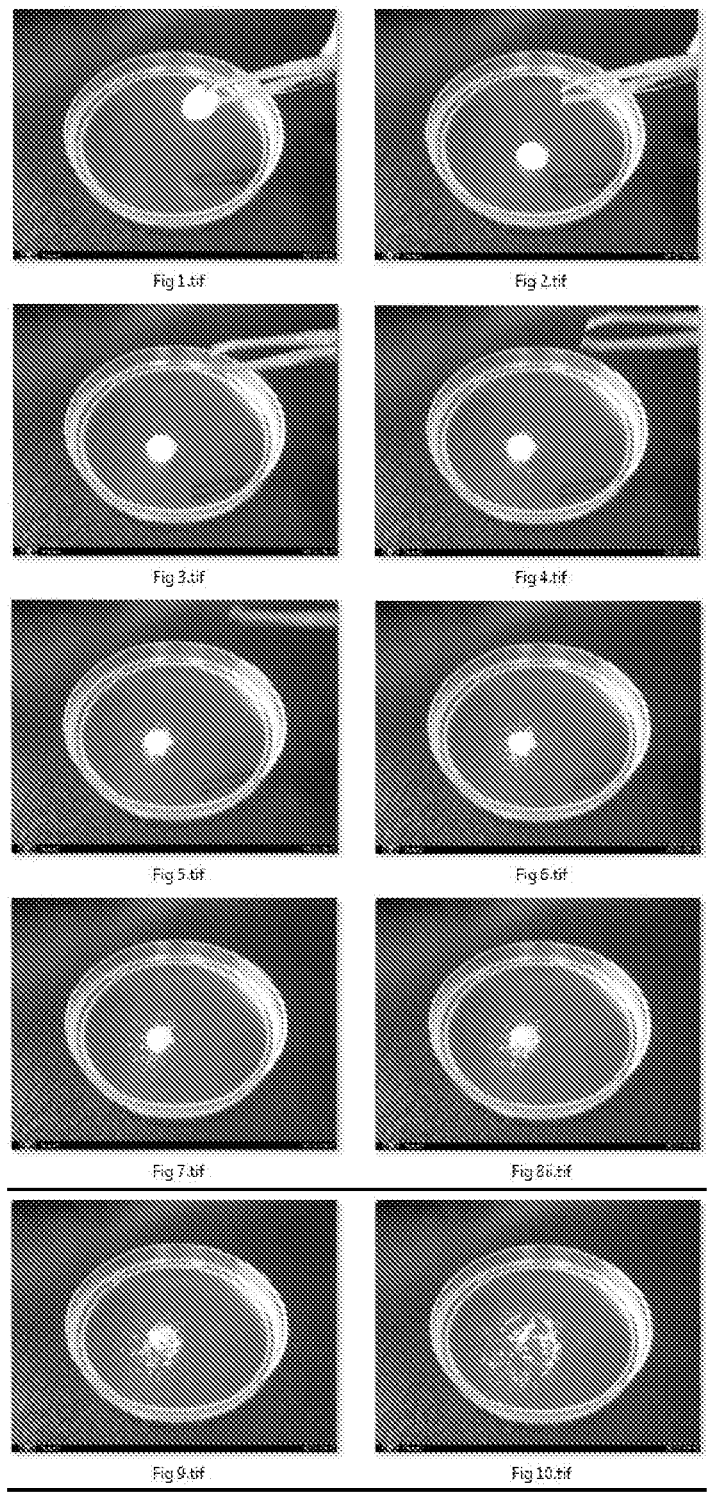
FIG. 9 shows visualization of the dissolution of Wafer 1 in accordance with the first aspect of the invention.
Figure 10:
FIG. 10 shows the size of the pharmaceutical dosage form of Wafer 2 in accordance with the second aspect of the invention (drug-free embodiment) compared to a one Rand coin.

| The salient features of the watered dosage form (Wafer 1) | |
|---|---|
| Feature | Ultra-fast disintegrating matrix system |
| Dispersion speed | ~1 second (FIG. 9) |
| Mouth feel | Non-gritty |
| Texture | Smooth |
| Dose size | <500 mg - insoluble<br><100 mg - soluble<br>*Adjustable to the requirements as cyclodextrin can be used to enclose the drug |
| Taste masking | Yes |
| Hygro-scopicity | Non-hygroscopic |
| Stability | Stable at room temperature and humidity condition as observed for 1 year (July 2011-July 2012) under South African climate conditions |
| Packaging | No special packaging required as the wafers can be dispensed on a poly-bottle with a dessicant, if required |
| Applications | An oral wafer matrix, a graft lubricant, a chromatography gel, a wound dressing, a mesh, a degradable bone fixation glue, a degradable ligament glue and sealant, a tendon implant, a dental implant, a reconstituted nerve injectable, a disposable article, a disposable contact lens, an ocular device, a rupture net, a rupture mesh, an instant blood bag additive, an instant haemodialysis additive, an instant peritoneal dialysis additive, an instant plasmapheresis additive, an inhalation drug delivery device, a cardiac assist device, a tissue replacing implant, a drug delivery device, an endotracheal tube lubricant, a drain additive, and a dispersible suspension system. |

Example 2

Wafer 2

A representative Example of the invention according to the second aspect of the invention was manufactured as described, illustrated and exemplified below.

In an embodiment of the second aspect of the invention the pharmaceutical dosage form was manufactured to be a multi-constituent system displaying, in use, ultra-rapid disintegration, the dosage form being formed into a wafer and comprising:
    i. a soluble matrix forming polymer, preferably hydroxypropyl cellulose (HPC);
    ii. an ester containing derivative of an acrylic polymer, preferably sodium polyacrylate;
    iii. an anti-collapsing agent, preferably diglycine;
    iv. a filler substance, preferably maltodextrin; and
    v. a taste masking agent and API, preferably hydroxypropyl-beta-cyclodextrin HPβCD-active pharmaceutical ingredient (API) inclusion complex (HPβCD-API inclusion complex).

A placebo may also be manufactured by simply excluding item (v) above during the manufacturing process. However, it is to be understood that placebos may include a taste masking agent without API.

Materials

Hydroxypropyl cellulose (KLUCEL®, Type: EF, Hercules Incorporated, Wilminton, Del., USA); Maltodextrin (Dextrose equivalent 16.5-19.5, Sigma-Aldrich, St. Louis, Mo., USA); Sodium Polyacrylate (average $M_w$~2100 Da, Sigma-Aldrich, St. Louis, Mo., USA); Diglycine (Gly-Gly, Sigma-Aldrich, St. Louis, Mo., USA); Hydroxypropyl-β-Cyclodextrin (average $M_w$~1,460, Sigma-Aldrich, St. Louis, Mo., USA).

Methods

Preparation of Drug-HPβCD Complex for Wafer 2

A specified amount of drug and HPβCD (in a specified ratio to the API or drug) were dissolved in a common solvent (in which both the API and HPβCD were soluble), preferably deionized water, until clear solutions were obtained, preferably at the saturation solubility of the API. The resulting HPβCD-API inclusion complex solution so obtained was frozen at −82° C. for 12 hours followed by lyophilization at 25 mtorr/−42° C./12 hours (FreeZone® 2.5, Labconco®, Kansas City, Mo., USA). The lyophilized sample was pulverized and stored for further use in a desiccator.

Preparation of Wafer Matrix Dosage Form in Accordance with a Second Aspect of the Invention:

A specified quantity of hydroxypropyl cellulose was dissolved in deionized water to make a clear solution 1. Thereafter, specified quantities of maltodextrin, sodium polyacrylate, and diglycine were added to solution 1 and stirred to complete solubilisation to form solution 2. A specified quantity of hydroxypropyl-β-cyclodextrin-API (drug) inclusion complex was added to solution 2 as the last addition to obtain solution 3. The solution 3 obtained above was filtered to remove any particulate matter and frozen at −82° C. for 12 hours followed by lyophilization at 25 mtorr/−42° C./5 hours to obtain the final dosage form.

A placebo (or drug-free (DF)) wafer was manufactured by omitting the step of adding hydroxypropyl-β-cyclodextrin-API (drug) inclusion complex to solution 2. The formulation of prepared placebo wafers is provided below in Table 6a (Formulation 1).

A drug-loaded (DL) wafer was prepared as described above wherein the API was rizatriptan benzoate, and the formulation thereof is provided below in Table 6b (Formulation 2).

A drug-loaded (DL) wafer was prepared as described above wherein the API was fluoxetine hydrochloride, and the formulation thereof is provided below in Table 6c (Formulation 3).

TABLE 6a

Formulation 1- Placebo (DF) of Wafer 2

| | |
|---|---|
| Hydroxypropyl cellulose | 0.5% w/v |
| Maltodextrin | 5.0% w/v |
| Sodium Polyacrylate | 0.25% w/v |
| Diglycine | 0.25% w/v |
| Hydroxypropyl-β-Cyclodextrin | 1.0% w/v |

TABLE 6b

Formulation 2- Rizatriptan benzoate loaded (DL) Wafer 2 (per wafer)

| | |
|---|---|
| Hydroxypropyl cellulose | 0.5% w/v |
| Maltodextrin | 5.0% w/v |
| Sodium Polyacrylate | 0.25% w/v |
| Diglycine | 0.25% w/v |
| Hydroxypropyl-β-Cyclodextrin | 1.0% w/v |
| Rizatriptan benzoate | 14.53 mg |
| Deionized water q.s. | 0.4 mL |

TABLE 6c

Formulation 3- Fluoxetine Hydrochloride loaded (DL) Wafer 2 matrix

| | |
|---|---|
| Hydroxypropyl cellulose | 0.5% w/v |
| Maltodextrin | 5.0% w/v |
| Sodium Polyacrylate | 0.25% w/v |
| Diglycine | 0.25% w/v |
| Hydroxypropyl-β-Cyclodextrin | 1.0% w/v |
| Fluoxetine Hydrochloride | 11.22 mg |
| Deionized water q.s. | 0.4 mL |

Figure 12:
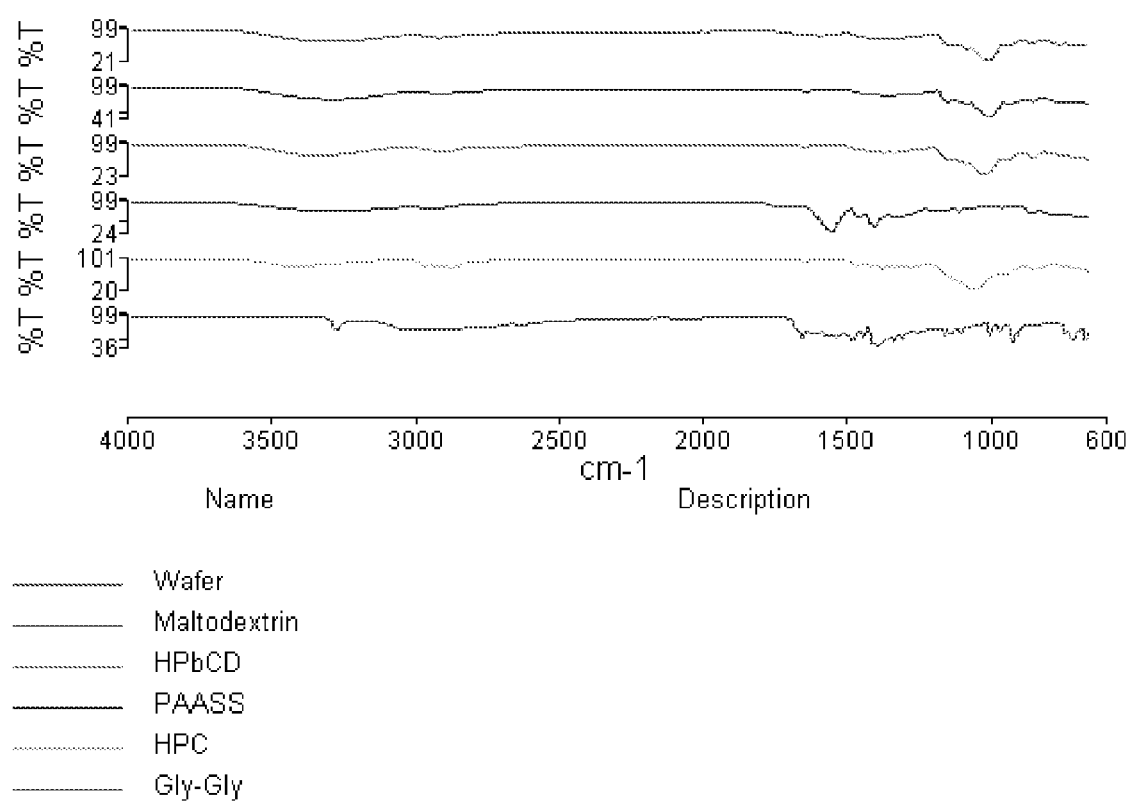
FIG. 12 shows a Fourier Transform Infra-Red spectra of the wafer matrix of Formulation 1 (a drug-free embodiment of the second aspect of the invention) and the inherent components.

FTIR Spectral Analysis of the Placebo Wafer of Formulation 1 (DF Wafer 2):

The FTIR spectra of all the constituent components and the wafer of Formulation 1 are depicted in FIG. 12. A detailed analysis of the unique and general contribution of the components to the formation of final structure can be elucidates as shown in Table 7 and as discussed below:

1. It is evident from FTIR analysis that all the components are uniformly distributed in the matrix system irrespective of the concentration of the component as all the components contributed to the generation of transmittance spectra with Maltodextrin forming the major part of the matrix-bulk filler.
2. The broad peak contribution of sodium polyacrylate (3308 $cm^{-1}$) confirms its role as the ester polymer coating the granular matrix rather than being the inherent matrix itself.
3. The highly prominent band at 1373 $cm^{-1}$ arising from the CH bending vibration in cellulose confirmed the intact presence of the cellulosic structure and hence the robustness of the wafer can be assured.
4. The presence of diglycine characteristic peak (—$CH_2$—$CH_2$—) in the finger print region (704 $cm^{-1}$) and also in the aliphatic region (2923 $cm^{-1}$) fulfils the hydrophobicity condition (among the all-hydrophillic system involved in lyophilization) required for the anti-collapsing micro-hardening property of diglycine in the final formulation.
5. The ubiquitous presence of hydroxyporpyl-b-cyclodextrin along the polymeric matrix encourages the fact that the drug will be uniformly dispersed once complexed with the cyclodextrin thereby providing adequate release. Given the short time of disintegration of the matrix; this might appear insignificant.
6. The shifting and change in intensity of various transmittance peaks along with the occurrence of a peak at 1590 $cm^{-1}$ confirms the formation of a unique blend having all the inherent functionalities of the components as well as a novel interaction profile of the components.

TABLE 7

FTIR spectral analysis of the wafer of Formulation 1 with respect to the component polymers (DF Wafer 2)

| S. No. | Wavelength Number for W1 | Corresponding wavelength number of the component(s) |
|---|---|---|
| 1. | 3308 $cm^{-1}$ | Sodium polyacrylate (3306 $cm^{-1}$) |
| 2. | 2922 $cm^{-1}$ | Diglycine (2923 $cm^{-1}$) |
| | | Hydroxypropyl-β-cyclodextrin (2925 $cm^{-1}$) |
| | | Maltodextrin (2923 $cm^{-1}$) |
| 3. | 1590 $cm^{-1}$ | Unique to the wafer system |
| 4. | 1373 $cm^{-1}$ | Hydroxypropyl cellulose (1373 $cm^{-1}$) |
| 5. | 1148 $cm^{-1}$ | Hydroxypropyl-β-cyclodextrin (1148 $cm^{-1}$) |
| | | Maltodextrin (1147 $cm^{-1}$) |
| 6. | 1077 $cm^{-1}$ | Hydroxypropyl-β-cyclodextrin (1079 $cm^{-1}$) |
| | | Maltodextrin (1076 $cm^{-1}$) |
| 7. | 995 $cm^{-1}$ | Maltodextrin (991 $cm^{-1}$) |
| 8. | 930 $cm^{-1}$ | Maltodextrin (927 $cm^{-1}$) |

TABLE 7-continued

FTIR spectral analysis of the wafer of Formulation 1 with
respect to the component polymers (DF Wafer 2)

| S. No. | Wavelength Number for W1 | Corresponding wavelength number of the component(s) |
|---|---|---|
| 9. | 848 cm$^{-1}$ | Maltodextrin (847 cm$^{-1}$) Hydroxypropyl-β-Cyclodextrin (848 cm$^{-1}$) |
| 10. | 758 cm$^{-1}$ | Maltodextrin (758 cm$^{-1}$) Hydroxypropyl-β-cyclodextrin (755 cm$^{-1}$) |
| 11. | 704 cm$^{-1}$ | Diglycine (706 cm$^{-1}$) |

Optical Microscopy Analysis of the Developed Wafer of Formulation 1 (DF Wafer 2)

Figure 13:
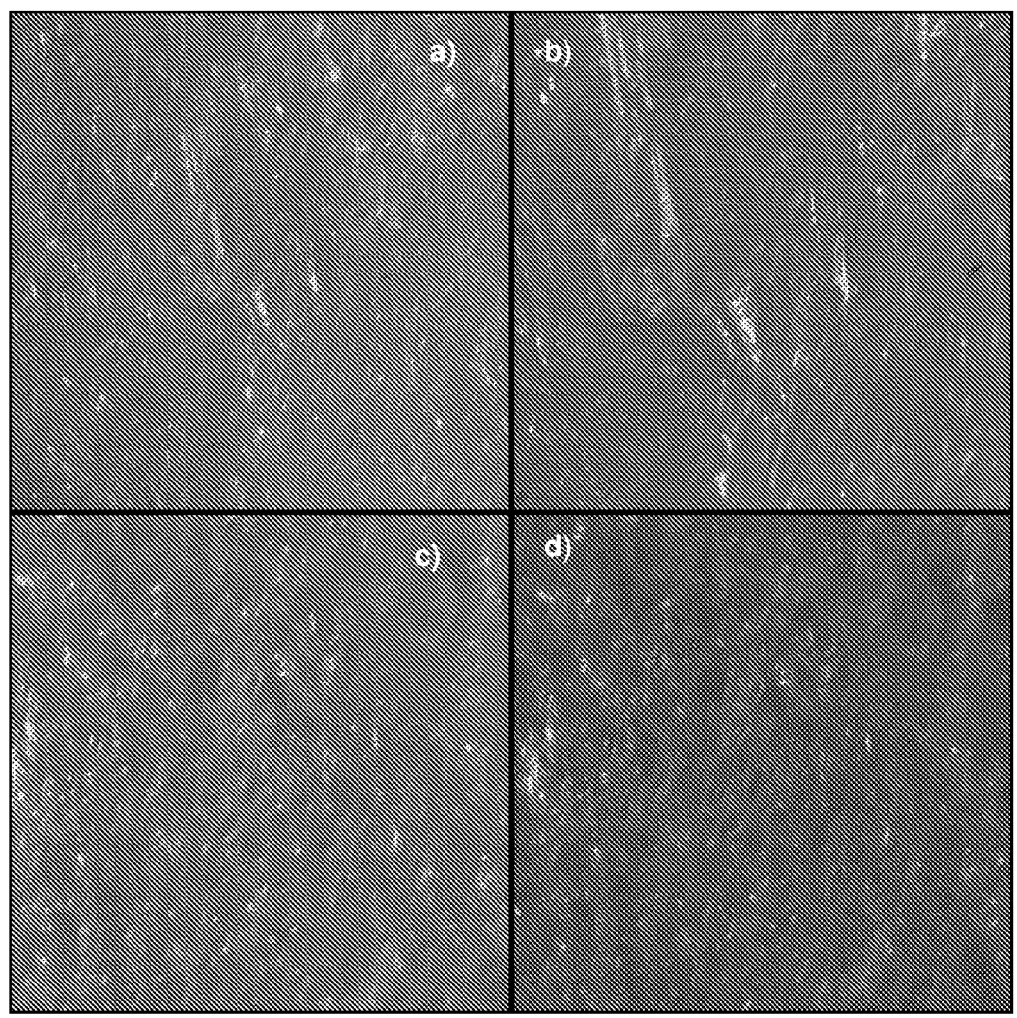
FIG. 13 shows photomicrographs showing a) and b) the surface of the wafer matrices of Formulation 1 (a drug-free embodiment of the second aspect of the invention); c) and d) the horizontal cross-sectional porous structure of the wafer matrices.
Figure 14:
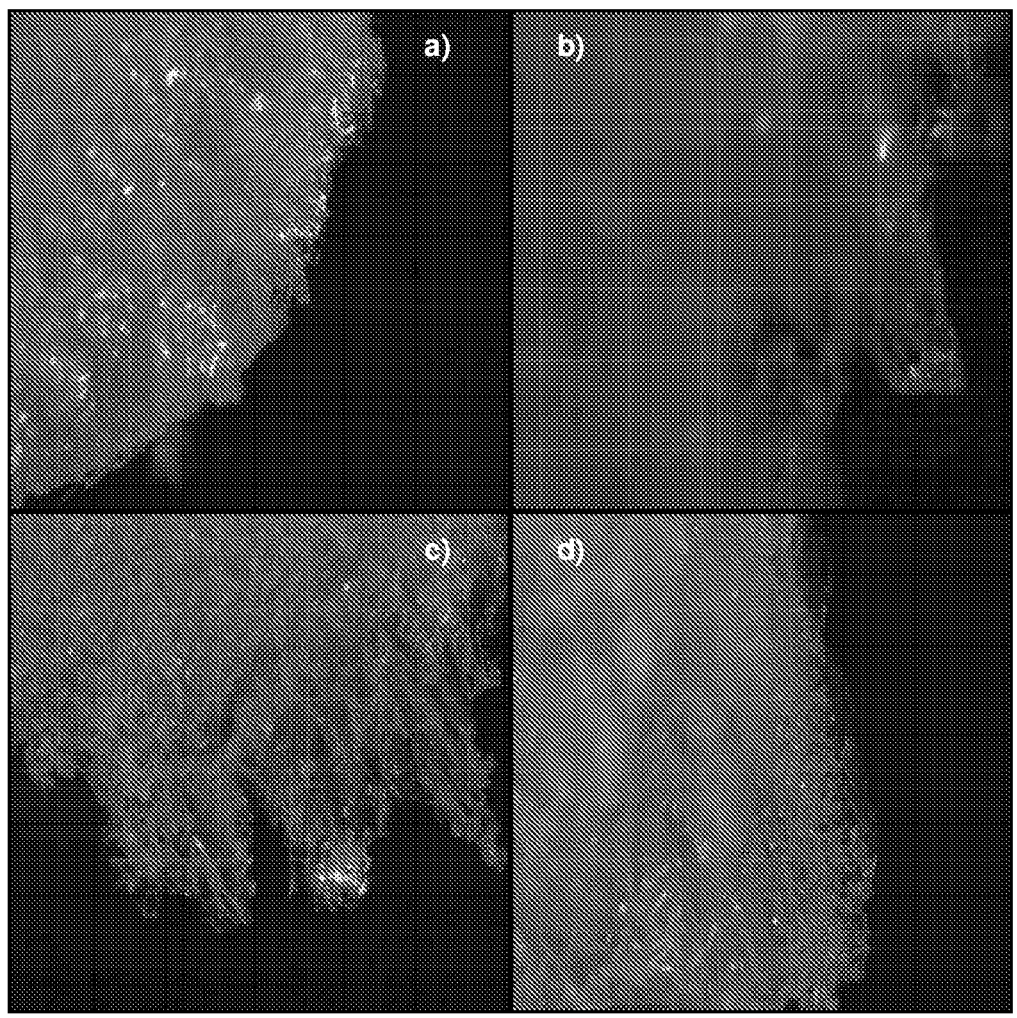
FIG. 14 shows photomicrographs showing a) and b) the layered structure vertically; c) and d) the connected fibrous structure of the wafer matrices of Formulation 1 (a drug-free embodiment of the second aspect of the invention) (vertical cross-section)

As depicted in FIG. 13 and FIG. 14; it can be concluded that:
1. The upper surface (the surface from which the water phase escaped during lyophilization) was crystalline in appearance: the surface structure is likely to disperse amongst the constituents microcrystalline environment leading to separation of these parts as soon as the aqueous phase makes a contact with the wafer matrix (FIG. 13a and FIG. 13b).
2. The horizontal cross-sectional area is highly porous with the pore size ranging from macro- to micropores: this continuous porous structure is likely to help in rapid ingress of aqueous phase leading to dispersion as well as dissolution of the matrix structure (FIG. 13c and FIG. 13d).
3. For taking the photomicrographs of FIG. 14; the matrix or wafer structure was broken to visualise the vertical cross-section. The matrix structure appeared layered in nature: this layer-by-layer structure is likely to assist the aqueous phase to disperse the matrix structure stage-by-stage leading to independent dispersion and dissolution of one layer with respect to other. This divides the matrix structure into various microstructures to be acted upon by the ingressing aqueous phase. Additionally, these independent microstructures will ensure the rapid disintegration of matrix structure independent of the size of the final formulation (FIGS. 14a and 14b).
4. FIGS. 14c and 14d display the micrograph inherent to a single layer in the matrix structure: the fibrous nature of the polymer composite can be visualized in the micrograph further explaining the robustness and connectivity of the matrix structure.

Scanning Electron Microscopy Analysis of the Wafer Matrix of Formulation 1 (DF Wafer 2)

Figure 15:
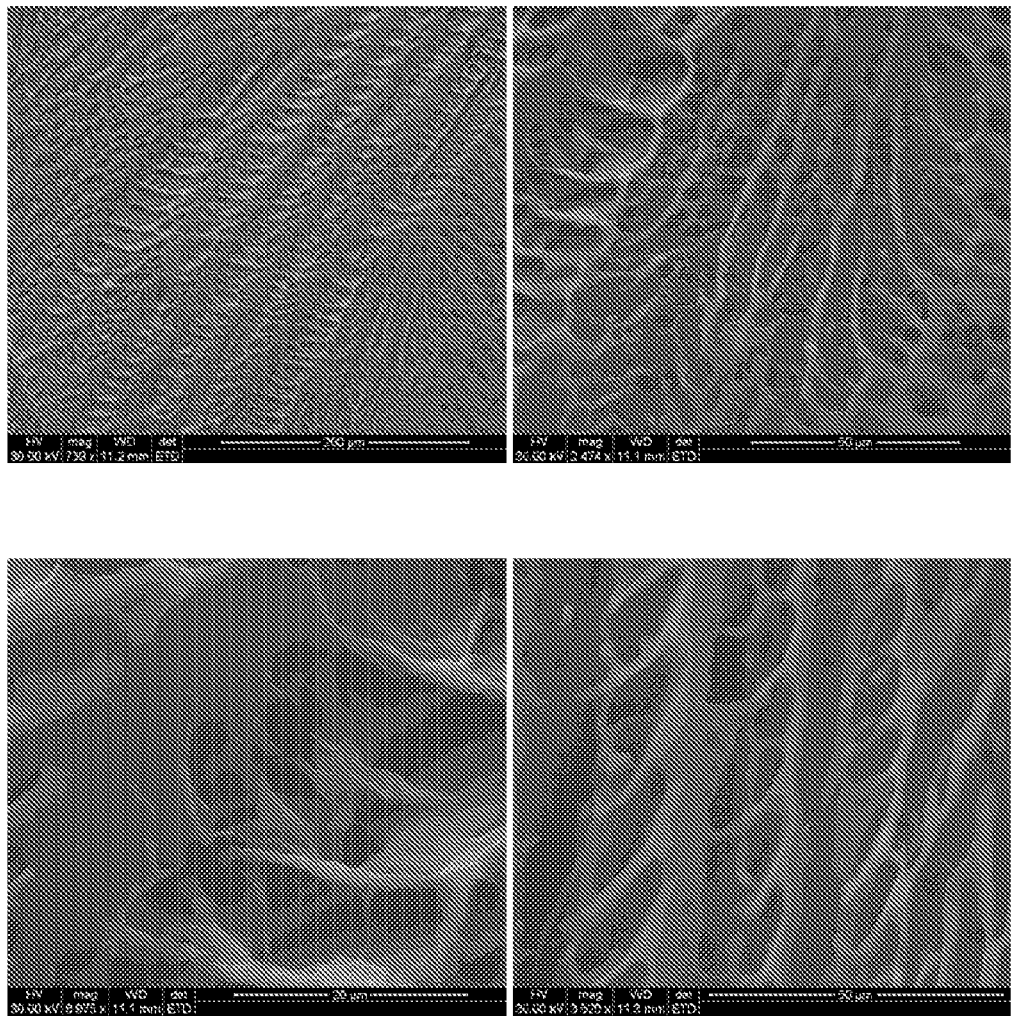
FIG. 15 shows scanning electron micrographs for the top surface of the wafer of Formulation 1 (a drug-free embodiment of the second aspect of the invention) at various magnifications.
Figure 16:
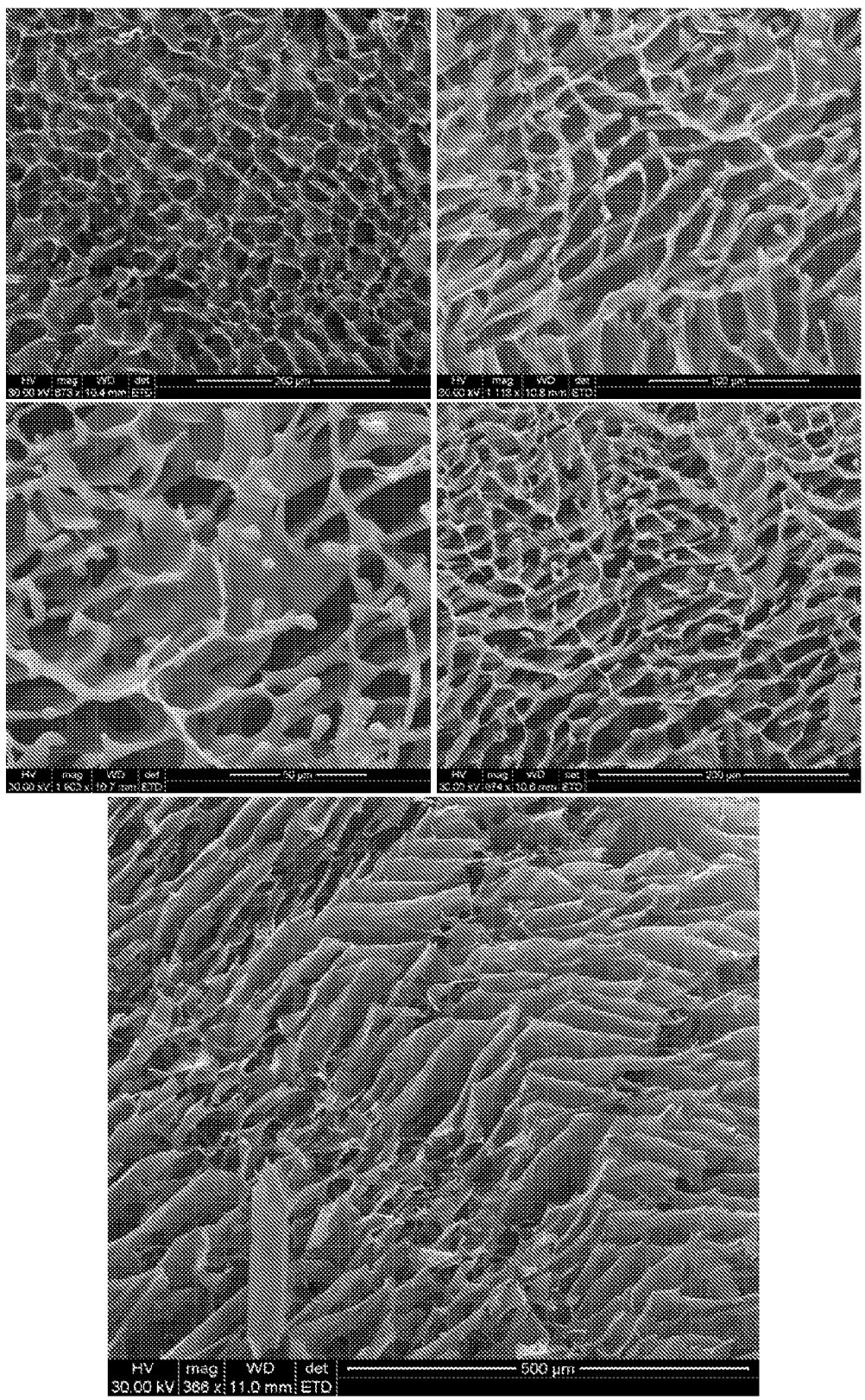
FIG. 16 shows scanning electron micrographs for the bottom surface of the wafer of Formulation 1 (a drug-free embodiment of the second aspect of the invention) at various magnifications.
Figure 17:
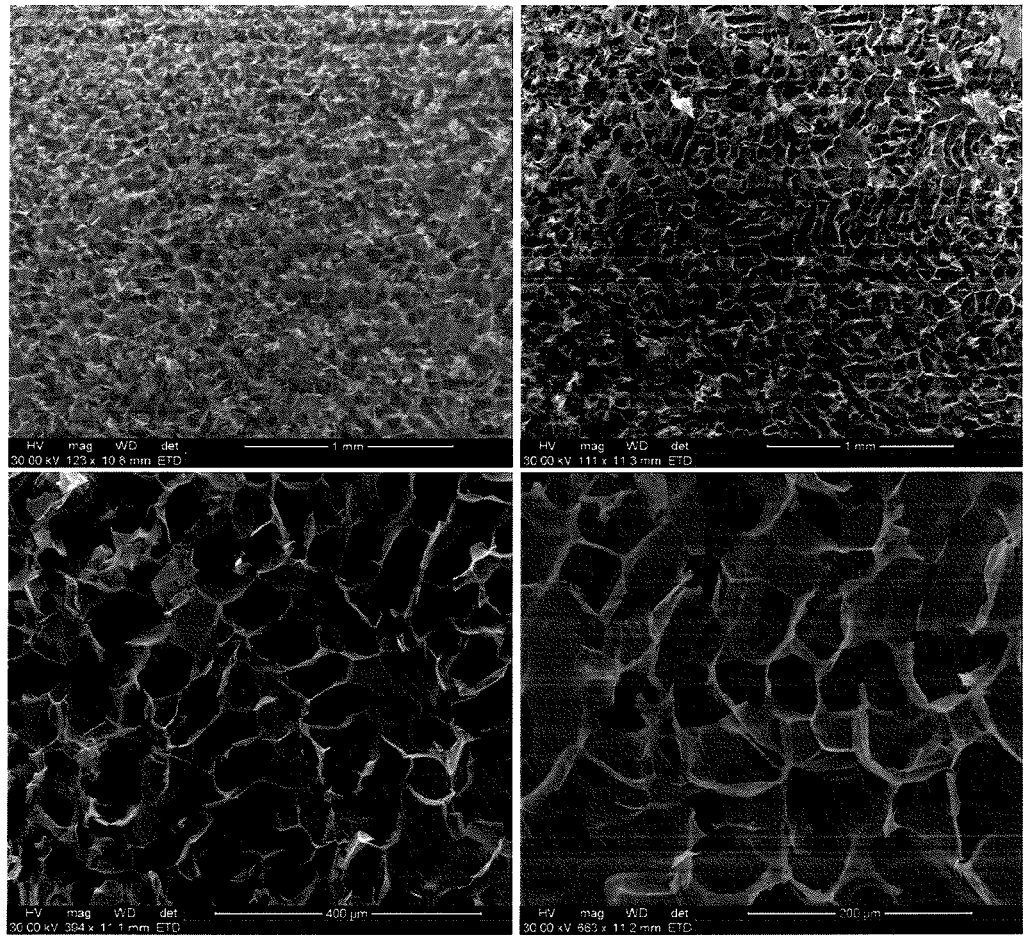
FIG. 17 shows Scanning electron micrographs for the cross-section of the wafer of Formulation 1 (a drug-free embodiment of the second aspect of the invention) at various magnifications.

The top surface electron microscopy scan of the wafer system of Formulation 1 displayed a unique highly porous-symmetrical-channelled structure (FIG. 15). On further magnification, the SEM micrograph showed that the channels are lined parallel with inter- and intra-channel connectivity. These channels further continued into the matrix bulk structure perpendicularly as evident from the SEM micrograph of the bottom surface of the wafer (FIG. 16). A closer view at the surface reveals that the symmetrical-channelled structure consisted of very deep thin-walled microporous architecture (pore width approximate 50 μm) going to full width of the wafer matrix. Additionally, the porous architecture of the matrix displayed an angled morphology which imparted the much needed matrix resilience to the wafers. The full-width continuity of the matrix was further proved by the scanning the cross-section of the wafer matrix (FIG. 17) which confirmed the vertical continuity-symmetry-linearity of the porous architecture and hence the no-resistance characteristic of the matrix towards water inflow and ingress.

X-Ray Diffraction Analysis of the Wafer Matrix of Formulation 1 (DF Wafer 2)

The influence of the constituent components on the performance of the wafer of Formulation 1 was analyzed using XRD analysis. In addition to the final product, XRD analysis was performed on the individual excipients hydroxypropyl cellullose, maltodextrin, sodium polyacrylate, diglycine, and Hydroxypropyl-β-Cyclodextrin. The XRD spectra clearly show that diglycine is a crystalline substance while hydroxypropyl cellulose, maltodextrin, sodium polyacrylate, and hydroxypropyl-β-cyclodextrin displayed amorphous nature. However; the final product—the wafer of Formulation 1—demonstrated primarily amorphous and partial crystalline nature. As maltodextrin constituted the bulk of the matrix (5.0%); the XRD curve of the final wafer formulation can be seen as a derivative of maltodextrin curve—leading to a remapping of maltodextrin due to the addition of specialized excipients for the wafer application. Maltodextrin displayed a broad peak (2θ=8.1-31.7) at an intensity of approximately 6547 at 2θ=18.55 which was reduced to approximately 5007 in the final product. This decrease in intensity of 2θ=8.1-31.7 degrees peak in maltodextrin can be attributed to the addition of sodium polyacrylate as sodium polyacrylate show a peak of intensity approximately 3876 at 2θ=18.55 as compared to hydroxypropyl cellullose and hydroxypropyl-β-cyclodextrin showing intensities of approximately 11688 and approximately 700, respectively. This confirms the role of sodium polyacrylate in imparting amorphousness to the final product. Additionally the peak width decreased from 2θ=8.1-31.7 to 2θ=10.34-28.73 which can be attributed to the crystalline nature of diglycine in the range of 2θ=20-30. The peak at 2θ=10.34-28.73 also corresponds to the peaks observed in hydroxypropyl cellullose and hydroxypropyl-β-cyclodextrin showing intensities of approximately 11688 and approximately 9700, respectively, ascertaining the overall conversion of partial crystallanity of hydroxypropyl cellullose and Hydroxypropyl-β-Cyclodextrin to amorphous nature. A small but significant peak was observed at 2θ=8.5 (intensity approximately 3007) which can be assigned to 2θ=8.23 (intensity≈13488) and 2θ=11.33 (intensity approximately 7105) peaks of hydroxypropyl cellulose and hydroxypropyl-β-cyclodextrin confirming their presence in the matrix system with an increase in amorphousness as the intensity of these peaks is drastically decreased. After lyophilisation, few very small signals are seen throughout the wafer spectra, indicating that some parts of the freeze dried product are still crystalline. One of the signals, at an angle of approximately 2θ=81.08 (intensity approximately 2126), is not present in any other sample. This new signal at 2θ=81.08 and the change in peak intensity, height, and width at 2θ=10.34-28.73 signal can be assigned to the unique polymorphic structure of maltodextrin, formed in presence of diglycine and sodium polyacrylate and due to water contact. This makes the wafer system a partial amorphous-partial crystalline matrix system providing the desired matrix solubility and stability. It is the unique combination of components comprising the Wafer 2 that allows for channels, typically parallel channels, to be formed. These channels facilitate rapid ingress of water and rapid disintegration and/or dissolution in use, and were surprising and expected physico-mechanical features of the Wafer 2.

Figure 18:
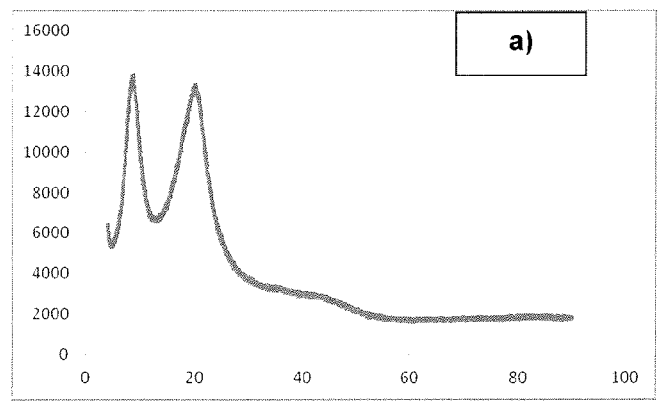
FIG. 18 shows X-Ray diffraction patterns of a) hydroxypropyl cellulose, b) hydroxypropyl-β-cyclodextrin, c) diglycine, d) sodium polyacrylate, e) maltodextrin, and f) the final wafer product of Formulation 1 (a drug-free embodiment of the second aspect of the invention). X-axis corresponds to 2θdegrees and Y-axis corresponds to intensity values.

FIG. 18 shows X-Ray diffraction patterns of hydroxypropyl cellulose (HPC), hydroxyl-β-cyclodextrin (HPβCD), diglycine, sodium polyacrylate, maltodextrin, and the final wafer product (Formulation 1—a drug-free embodiment of the second aspect of the invention).

Textural Analysis of the Wafer Matrix of Formulation 1 (DF Wafer 2)

The textural analysis of the matrix at various force (5N and 10 N), strain (10% and 25%), and displacement (2 mm) conditions was carried out on a texture analyzer (TA.XT plus, Stable Micro Systems, UK) using a flat-base cylindrical probe (10 mm in diameter) to ascertain the robustness of the wafer matrix. The matrix structure was intact at all these conditions and displayed a high matrix deformation energy, rigidity gradient and matrix resilience at force (5N and 10 N), strain (5% and 25%), and displacement (2 mm) conditions, as shown in Table 4.

TABLE 8

Textural profiling for physicochemical characterization of the wafer matrices of Formulation 1 (DF Wafer 2)

| Texture analysis mode | | Deformation energy (J) | Matrix Hardness (N/mm$^2$) | Matrix resilience (%) |
|---|---|---|---|---|
| Strain (%) | 10 | 0.425 | 9.769 | 15.437 |
| | 25 | 3.980 | 16.088 | 09.046 |
| Force (N) | 5 | 0.795 | 17.446 | 17.000 |
| | 10 | 1.312 | 25.222 | 19.721 |
| Distance (mm) | 2 | 24.016 | 12.644 | 03.608 |

FIG. 19 shows typical force distance and force time profiles of the wafer matrix of Formulation 1 (a drug-free embodiment of the second aspect of the invention) at distance mode for determining (a) matrix hardness (determined from gradient between anchors 1 and 2) and deformation energy (determined from AUC between anchors 1 and 2) and (b) matrix resilience.

FIG. 20 shows typical force distance and force time profiles of the wafer matrix (of Formulation 1—a drug-free embodiment of the second aspect of the invention) at strain mode for determining (a) matrix hardness (determined from gradient between anchors 1 and 2) and deformation energy (determined from AUC between anchors 1 and 2); and (b) matrix resilience.

FIG. 21 shows typical force distance and force time profiles of the wafer matrix (of Formulation 1—a drug-free embodiment of the second aspect of the invention) at force mode for determining (a) matrix hardness (determined from gradient between anchors 1 and 2) and deformation energy (determined from AUC between anchors 1 and 2); and (b) matrix resilience.

Porositometric quantification of the developed wafer matrices of Formulation 1 (DF Wafer 2)

Surface Area

| | |
|---|---|
| Single point surface area at P/Po = 0.200637096: | 1.9615 m$^2$/g |
| BET Surface Area: | 2.6956 m$^2$/g |
| t-Plot External Surface Area: | 4.2946 m$^2$/g |
| BJH Adsorption cumulative surface area of pores between 17.000 Å and 3000.000 Å diameter: | 2.625 m$^2$/g |
| BJH Desorption cumulative surface area of pores between 17.000 Å and 3000.000 Å diameter: | 2.5504 m$^2$/g |

Pore Volume

| | |
|---|---|
| Single point adsorption total pore volume of pores less than 808.805 Å diameter at P/Po = 0.975468283: | 0.003604 cm$^3$/g |
| t-Plot micropore volume: | −0.000998 cm$^3$/g |
| BJH Adsorption cumulative volume of pores between 17.000 Å and 3000.000 Å diameter: | 0.005569 cm$^3$/g |
| BJH Desorption cumulative volume of pores between 17.000 Å and 3000.000 Å diameter: | 0.005528 cm$^3$/g |

Porositometric quantification of the developed wafer matrices of Formulation 1 (DF Wafer 2)

Pore Size

| | |
|---|---|
| Adsorption average pore width (4V/A by BET): | 53.4764 Å |
| BJH Adsorption average pore diameter (4V/A): | 84.867 Å |
| BJH Desorption average pore diameter (4V/A): | 86.694 Å |

FIG. 22 shows a) a linear isothermic plot, b) a Log isothermic plot, c) a linear BJH adsorption dV/dD curve for pore volume, and d) a log BJH adsorption dV/dD curve for pore volume of the composite polymeric matrices. The FIGS. 12 a-d confirm the presence of a "H4 hysteresis" of the isotherm.

TABLE 9

The salient features of the Ultra-fast or rapid disintegrating matrix system of Formulation 1 (DF Wafer 2)

| Feature | Ultra-fast disintegrating matrix system |
|---|---|
| Dispersion speed | ~1 second |
| Mouth feel | Non-gritty |
| Texture | Smooth |
| Dose size | <500 mg - insoluble<br><100 mg - soluble<br>*Adjustable to the requirements as cyclodextrin can be used to enclose the drug |
| Taste masking | Yes |
| Hygroscopicity | Non-hygroscopic |
| Drug assay (%) | Rizatriptan benzoate wafers: 96.32 ± 1.82<br>Fluoxetine HCl wafers: 97.24 ± 3.23 |
| Stability | Stable at room temperature and humidity condition as observed for 1 year (July 2011-July 2012) under South African climate conditions |
| Packaging | No special packaging required as the wafers can be dispensed on a poly-bottle with a dessicant, if required |
| Applications | An oral wafer matrix, a graft lubricant, a chromatography gel, a wound dressing, a mesh, a degradable bone fixation glue, a degradable ligament glue and sealant, a tendon implant, a dental implant, a reconstituted nerve injectable, a disposable article, a disposable contact lens, an ocular device, a rupture net, a rupture mesh, an instant blood bag additive, an instant haemodialysis additive, an instant peritoneal dialysis additive, an instant plasmapheresis additive, an inhalation drug delivery device, a cardiac assist device, a tissue replacing implant, a drug delivery device, an endotracheal tube lubricant, a drain additive, and a dispersible suspension system. |

Mechanism of Performance of the Matrix System of Formulation 1 (DF Wafer 2)

The performance of this ultra-fast disintegrating matrix system can be summarised in following points:

1. The constituent polymers and excipients used in the fabrication of the matrix are hydrophilic and freely soluble in aqueous media and hence impart rapid and complete dissolution and solubilisation of the matrix system.
2. The addition of sodium polyacrylate and diglycine provided the much needed amorphous-crystalline balance to the wafer matrix further responsible for the enhanced solubility of the combination over the individual components as well as the much required robustness and stability of the solid matrix further proven by the texture analysis results.
3. The scanning electron micrographs displayed a microporous-symmetrical-angled morphology capable of imparting a resistance-free and laminar flow of water into the matrix leading to rapid disintegration and subsequent dissolution of the matrix. The angled morphology additionally contributed to the much needed matrix resilience of the final product.

The invention claimed is:

1. A compound of the Formula (I):

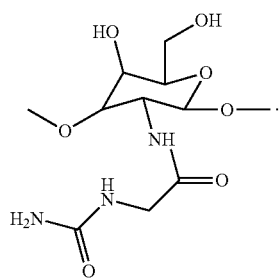

Formula (I)

2. A pharmaceutical dosage form comprising:
a compound of the formula (I)

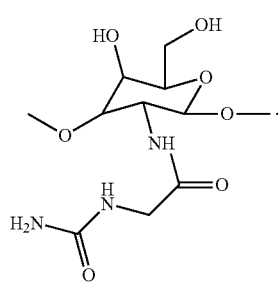

Formula (I)

Wherein the compound of the formula (I) is termed carbamoyl glycinated chitosan (CmGC);
a soluble matrix polymer in the form of hydroxypropyl cellulose (HPC);
an ester containing derivative of an acrylic polymer in the form of sodium polyacrylate;
an anti-collapsing agent in the form of diglycine; and
a filter substance in the form of maltodextrin.

3. The pharmaceutical dosage form according to claim 2, further comprising a soluble matrix forming polymer, wherein the soluble matrix forming polymer is at least one natural and/or synthetic polymer selected from the group: polyanionic polysaccharides, carboxymethyl cellulose, carboxymethyl amylose, chondroitin-6-sulfate, dermatin sulfate, heparin, heparin sulfate, collagen, fibrinogen, albumin, fibrin, chitosan, hyaluronic acid, polyvinylpyrrolidone, poly(vinyl alcohol) and its derivatives, poly(ethylene glycol) and its derivatives, pluronics, poloxamers, tetronics, polybutylene oxide, poly(ethylene oxide), poly(propylene oxide), poly(ethylene oxide)-oxide)-poly(propylene oxide)-poly(ethylene oxide), poly(vinyl acetate), poly(vinyl amine), pectin, carrageenan, dextran sulfate, polylysine, gelatin, carboxymethyl chitin, dextran, agarose, pullulan, a starch derivative, preferably the soluble matrix polymer is a hydroxyalkylated starch derivative, more preferably, hydroxypropyl cellulose (HPC).

4. The pharmaceutical dosage form according to claim 3, further comprising at least one ester containing derivative of an acrylic polymer selected from the group: poly(hydroxyethyl methylacrylate), hydroxypropyl methacrylamide-based copolymers, polyacrylamide, poly(methacrylic acid-grafted-ethylene glycol), poly(N-2-hydroxypropyl methacrylamide), poly(2-hydroxyethylmethacrylate), poly(acrylic acid), polyacrylamide, polyacrylonitrile, polycaprolactone, poly(ethylene imine), poly(ethyl methacrylate), propylene fumarate, poly(glucosylethyl methacrylate), poly(hydroxy butyrate), poly(hydroxyethyl methacrylate), poly(hydroxypropyl methacrylamide), and poly(methyl methacrylate) and their polyesters, preferably the ester containing derivative of an acrylic polymer is an ester derivative of polyacrylic acid, more preferably sodium polyacrylate.

5. The pharmaceutical dosage form according to claim 2, further comprising an anti-collapsing agent, preferably the anti-collapsing agent comprises an amino acid chain, more preferably the anti-collapsing agent comprises an amino acid chain having 1 amino acid residue, further preferably the anti-collapsing agent comprises an amino acid chain having 2 amino acid residues, most preferably the anti-collapsing agent is diglycine.

6. The pharmaceutical dosage form according to claim 2, further comprising at least one filler substance, in use binding and/or combining the various components comprising the dosage form, the filler substance being at least one compound selected from the group: maltodextrin (MD), dextrin; alkaline-modified starch; bleached starch; oxidized starch, enzyme-treated starch such as maltodextrin, cyclodextrin, monostarch phosphate, distarch phosphate by esterification, crosslinked starch, acetylated starch, hydroxypropylated starch, hydroxyethyl starch, cationic starch, carboxymethylated starch, phosphated distarch phosphate, hydroxypropyl distarch phosphate, acetylated oxidized starch, preferably the filler substance is an enzyme treated/hydrolyzed starch, more preferably, maltodextrin.

7. The pharmaceutical dosage form according to claim 2, further comprising at least one taste masking agent, in use to mask the unsavoury taste of the dosage form, the taste masking agent selected from the group: macrocyclic compounds such as cyclodextrins and their derivatives, porphyrins, ion exchange resins, cucurbiturils, permeation enhancing agents and stabilizers, preferably the taste masking agent is hydroxypropyl-beta-cyclodextrin (HPβCD).

8. The pharmaceutical dosage form according to claim 2, further comprising an active pharmaceutical ingredient (API) selected from the group consisting of: smoking cessation drugs, narcotic analgesics, anesthetics, antitussives, normarcotic analgesics such as the nonsteroidal anti-inflammatory agents (NSAIDS), erectile dysfunction drugs, female sexual dysfunction drugs, antihistamines, cold and allergy drugs, drugs that combat cough, drugs that combat respiratory disorders, drugs that combat sore throat, drugs that combat heartburn and/or dyspepsia, antiemetics, sleep aids, drugs that combat diarrhea, drugs that improve oral hygiene, antagonists of CGRP receptors, drugs associated with migrane treatment, drugs for hormone replacement, drugs that combat Alzheimer's disease, sitagliptin, caffeine and caffeine salt compounds.

9. The pharmaceutical dosage form according to claim 2, further comprising a HPβCD-API inclusion complex consisting of an active pharmaceutical ingredient (API) incorporated within taste masking agent hydroxypropyl-beta-cyclodextrin (HPβCD).

10. A pharmaceutical dosage form comprising:
   a compound of Formula (I), (carbamoyl glycinated-chitosan);
   a soluble matrix forming polymer in the form of hydroxypropyl cellulose (HPC);
   an ester containing derivative of an acrylic polymer in the form of sodium polyacrylate;
   an anti-collapsing agent in the form of diglycine; and
   a filler substance in the form of maltodextrin.

11. The pharmaceutical dosage form according to claim 10, further comprising a taste masking agent in the form of hydroxypropyl-beta-cyclodextrin (HPβCD).

12. The pharmaceutical dosage form according to claim 10, further comprising an active pharmaceutical ingredient (API).

13. The pharmaceutical dosage form according to claim 10, further comprising a HPβCD-API inclusion complex consisting of a taste masking agent and an API.

14. The pharmaceutical dosage form according to claim 2, wherein the dosage form is formed into a wafer to be applied in use to mucosa lining the oral cavity of a human or animal such that the target site for release of the API is the mucosa lining the oral cavity.

15. A method of manufacturing the compound of formula (I) according to claim 1, the method comprising the steps of:
   (a) reacting chitosan with a hydantoin acid solution to form a solution;
   (b) dialyzing said solution;
   (c) freezing said dialyzing solution; and
   (d) lyophilizing the frozen solution.

16. The method according to claim 15, wherein prior to Step (b) the solution is centrifuged to remove any or all particulate matter, preferably the centrifuged solution is dialyzed against water, preferably deionized water.

17. The method according to claim 15, wherein Step (c) takes place at −82° C. for a certain period of time, preferably between 24 to 48 hours.

18. The method according to claim 15, wherein Step (d) takes place at 25 mtorr, −42° C., for between 12 to 48 hours.

19. A method of manufacturing the pharmaceutical dosage form according to claim 13 comprising the steps of:
   (a) dissolving a soluble matrix forming polymer, preferably hydroxy propyl cellulose (HPC), in a liquid medium, preferably deionized water to produce Solution 1;
   (b) adding to Solution 1 a soluble chitosan derivative polymer to produce Solution 2;
   (c) adding to Solution 2 a filler, preferably maltodextrin, an ester containing derivative of an acrylic polymer, preferably sodium polyacrylate and an anti-collapsing agent, preferably diglycine, to produce Solution 3;
   (d) adding to Solution 3 a taste-masking agent, preferably HPβCD-API inclusion complex, to produce Solution 4;
   (e) freezing Solution 4; and
   (f) lyophilizing the frozen Solution 4.

* * * * *